US010436018B2

(12) United States Patent
Kouchmeshky et al.

(10) Patent No.: US 10,436,018 B2
(45) Date of Patent: Oct. 8, 2019

(54) DOWNHOLE ELECTROMAGNETIC ACOUSTIC TRANSDUCER SENSORS

(71) Applicant: BAKER HUGHES INCORPORATED, Houston, TX (US)

(72) Inventors: Babak Kouchmeshky, Kingwood, TX (US); Xiaochu Yao, Houston, TX (US); Stanislav Forgang, Houston, TX (US); Pawel J. Matuszyk, Spring, TX (US); Marc S. Ramirez, Missouri City, TX (US); Otto N. Fanini, Houston, TX (US); Douglas J. Patterson, Magnolia, TX (US); Vimal Shah, Houston, TX (US)

(73) Assignee: Baker Hughes, a GE company, LLC, Houston, TX (US)

( * ) Notice: Subject to any disclaimer, the term of this patent is extended or adjusted under 35 U.S.C. 154(b) by 215 days.

(21) Appl. No.: 15/288,092

(22) Filed: Oct. 7, 2016

(65) Prior Publication Data

US 2018/0100387 A1    Apr. 12, 2018

(51) Int. Cl.
*G01N 29/24* (2006.01)
*G01N 29/34* (2006.01)
(Continued)

(52) U.S. Cl.
CPC .............. *E21B 47/091* (2013.01); *B06B 1/04* (2013.01); *B06B 1/045* (2013.01); *E21B 47/16* (2013.01);
(Continued)

(58) Field of Classification Search
CPC ........ E21B 47/091; E21B 47/16; E21B 47/14; B06B 1/04; B06B 1/045; G01N 29/2412;
(Continued)

(56) References Cited

U.S. PATENT DOCUMENTS 7,660,197 B2    2/2010  Barolak
8,553,494 B2   10/2013  Barolak
(Continued)

FOREIGN PATENT DOCUMENTS

| AU | 20140201937 A1 | * | 10/2014 | ............... H04R 9/04 |
| GB | 2515518 A | * | 12/2014 | ............... H04R 3/00 |
| JP | 2015040746 A | * | 3/2015 | ............. G01N 29/04 |

OTHER PUBLICATIONS

Lee, RF et al., "Coupling and Decoupling Theory and Its Application to the MRI Phased Array," Mag. Reson. Med. 48 pp. 203-213 (2002).

(Continued)

*Primary Examiner* — Lisa M Caputo
*Assistant Examiner* — Rose M Miller
(74) *Attorney, Agent, or Firm* — Mossman, Kumar & Tyler, P.C.

(57) ABSTRACT

Systems, devices, and methods for estimating a value of a downhole parameter of interest. Aspects include an apparatus for evaluating a tubular. The apparatus may include a sensor including an electromagnetic acoustic transducer (EMAT) device configured to be conveyed into the tubular. The EMAT device may include measurement circuitry comprising at least one conductive coil; and a magnet array comprising magnets arranged with a corresponding direction of magnetization of each magnet oriented according to a configuration producing a greater magnetic flux on a first side of the array than on a second side opposing the first side. The magnetic flux produced from the second side may be substantially zero. In embodiments, the configuration of magnets comprises at least a first set of permanent magnets in a linear Halbach configuration.

18 Claims, 22 Drawing Sheets

(51) Int. Cl.
*E21B 47/09* (2012.01)
*G01V 1/52* (2006.01)
*B06B 1/04* (2006.01)
*E21B 47/16* (2006.01)
*G01N 29/28* (2006.01)

(52) U.S. Cl.
CPC ......... *G01N 29/2412* (2013.01); *G01N 29/28* (2013.01); *G01N 29/34* (2013.01); *G01V 1/52* (2013.01); *G01N 2291/0421* (2013.01); *G01N 2291/0422* (2013.01); *G01N 2291/0423* (2013.01); *G01N 2291/0427* (2013.01)

(58) Field of Classification Search
CPC .................... G01N 29/28; G01N 29/34; G01N 2291/0421; G01N 2291/0422; G01N 2291/0423; G01N 2291/0427; G01N 2291/2636; G01V 1/52
USPC ................. 73/643, 623, 622, 152.57, 152.58
See application file for complete search history.

(56) References Cited

U.S. PATENT DOCUMENTS

| | | | | |
|---|---|---|---|---|
| 9,942,663 | B1* | 4/2018 | Salvatti | H04R 9/025 |
| 2008/0264624 | A1* | 10/2008 | Hall | G01V 3/26 166/66.5 |
| 2014/0160889 | A1 | 6/2014 | Barolak | |
| 2014/0177389 | A1* | 6/2014 | Bolshakov | E21B 47/0005 367/35 |
| 2016/0093429 | A1* | 3/2016 | Colich | H01F 7/0289 335/306 |
| 2016/0245779 | A1* | 8/2016 | Khalaj Annineh | E21B 47/00 |

OTHER PUBLICATIONS

Xu, Yang et al., "A New Structure of SH Wave Electromagnetic Acoustic Transducer (EMAT)," Acoustical Imaging, W. Arnold and S. Hirsekorn (eds), pp. 175-183 (2004).

Lopez, M.A., "Overlap Decoupling in Hole-Slotted Arrays," Proc. Intl. Soc. Mag. Reson. Med. 18, p. 3930 (2010).

Patterson, Douglas; Bolshakov, Alexei; and Matuszyk, Pawel, "Utilization of Electromagnetic Acoustic Transducers in Downhole Cement Evaluation," SPWLA 56th Annual Logging Symposium, 16 pp. (2015).

* cited by examiner

15 Magnets Baseline Design (15C)

FIG. 5A

45 Magnets Hyper Halbach Array1 (45H1)

FIG. 5B

25 Magnets Halbach Array (25H)

FIG. 5C

45 Magnets Hyper Halbach Array2 (45H2)

FIG. 5D

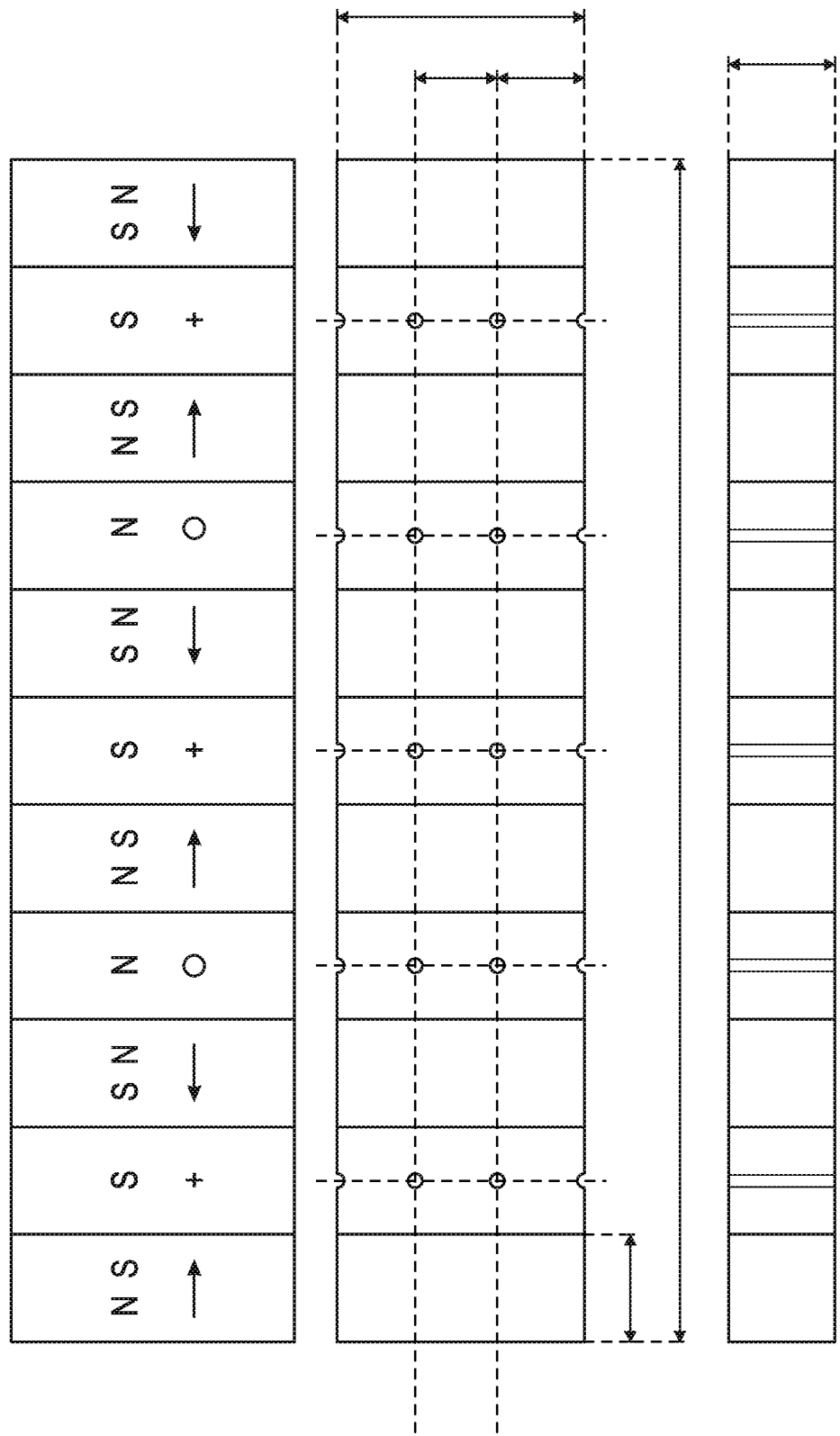

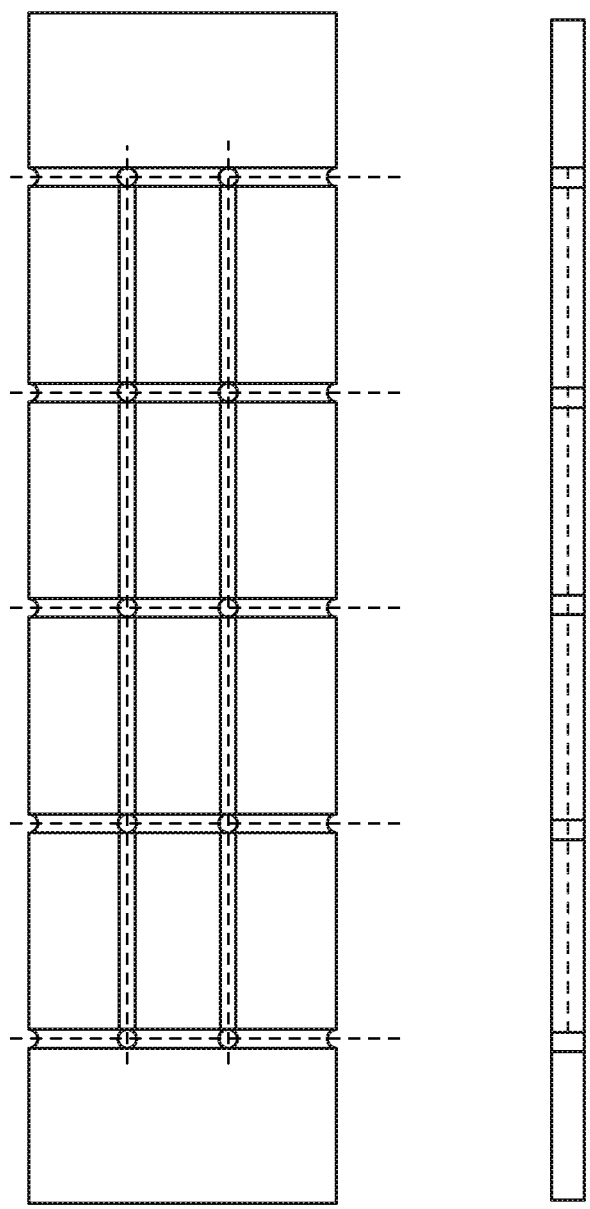

DOWNHOLE ELECTROMAGNETIC ACOUSTIC TRANSDUCER SENSORS

FIELD OF THE DISCLOSURE

The present disclosure is related to the field of investigating boreholes with electric wireline tools and Logging While Drilling (LWD) tools. More specifically, the present disclosure relates to a method and apparatus of producing and detecting acoustic forces within a wellbore casing to evaluate the integrity of the casing. General embodiments may relate to evaluating the integrity of bonds that adhere wellbore casing to a wellbore.

BACKGROUND OF THE DISCLOSURE

Electromagnetic-acoustic transducers (EMATs) have been used in non-destructive testing, including in the borehole, using well-understood physical phenomena. When a wire is placed near the surface of an electrically conducting object and is driven by a current at a suitable ultrasonic frequency, eddy currents are induced in a near surface region of the object. If a static magnetic field is also present, these eddy currents experience Lorentz forces. These forces cause an acoustic excitation in the object. In a reciprocal use, an electric signal will be generated in the wire as a result of acoustic excitation in a metal placed close to a permanent magnet. Attenuation and/or reflection of the acoustic waves bear information on the defects and surroundings of the object. An EMAT may be designed to produce a single waveform, such as shear horizontal waves (SH) or Lamb waves.

Electromagnetic-acoustic transducers (EMATs) have more recently been used downhole as components of downhole tools. The transducer periodically emits an acoustic energy pulse on command from a controller circuit in the tool. After emission of the acoustic energy pulse, the transducer can be connected to a receiving circuit, generally located in the tool, for measuring a returning echo of the previously emitted acoustic pulse which is reflected off the borehole wall. By processing the reflected signal, it is possible to infer something about the acoustic impedance characterizing the near-borehole environment. Specifically, changes in acoustic impedance are diagnostic of the geometry of the borehole.

As one example, it is known to conduct acoustic inspection of a casing cemented in a borehole to determine specific properties related to the casing and surrounding materials. For example, the bond between the cement and the casing may be evaluated, or the strength of the cement behind the casing or the casing thickness may be estimated using measurements of reflected acoustic waves, which may be generally referred to as casing cement bond logging

SUMMARY OF THE DISCLOSURE

Aspects of the present disclosure include an apparatus for evaluating a tubular. The apparatus may include a sensor including an electromagnetic acoustic transducer (EMAT) device configured to be conveyed into the tubular. The EMAT device may include measurement circuitry comprising at least one conductive coil; and a magnet array comprising magnets arranged with a corresponding direction of magnetization of each magnet oriented according to a configuration producing a greater magnetic flux on a first side of the array than on a second side opposing the first side. The magnetic flux produced from the second side may be substantially zero. In embodiments, the configuration of magnets comprises at least a first set of permanent magnets in a linear Halbach configuration.

The sensor may be further configured to propagate an acoustic wave in the tubular via generation of acoustic energy within the tubular. The at least one coil may include at least one transmitter coil; and at least one receiver coil electrically non-identical to the at least one transmitter coil. An inductance of the at least one transmitter coil may be lower than an inductance of the at least one receiver coil. The at least one transmitter coil may include multiple coil layers electrically connected in parallel. The at least one coil may comprise a plurality of coils, and the measurement circuitry may be configured to be switched between a transmit mode and a receive mode. While in the transmit mode, the measurement circuitry may form a first circuit optimized for transmission with at least some of the plurality of coils. While in the receive mode, the measurement circuitry may form a second circuit optimized for reception with a portion of the plurality of coils. In the transmit mode, the plurality of coils may include multiple coil layers electrically connected in parallel; in the receive mode, the plurality of coils may include the multiple coil layers electrically connected in series. The number of coil layers may be optimized to maximize the gain while taking into account magnet liftoff effects.

A coupling device may be utilized to optimize EMAT transducers for down hole measurements, especially attenuation measurements. In aspects, a receiving coil of the device may be configured to increase a signal-to-noise ratio and a measurement dynamic range for received signals. The device may be further configured to record an acoustic wave propagating in the tubular.

The EMAT device may be further configured to form a wave within the tubular, the wave having a polarization that is that of at least one of (i) a compressional wave, (ii) a shear wave, (iii) a transversely polarized shear wave, (iv) a Lamb wave, and (v) a Rayleigh wave. A maximum of the magnetic flux on the first side of the magnet array may be centered on a particular magnet of the magnet array. The at least one coil may comprise: at least one transmitter coil having a first alignment with respect to the particular magnet; and at least one receiver coil having a second alignment with respect to the particular magnet different than the first alignment. The at least one transmitter coil may comprise a perimeter, and a portion of the perimeter may be aligned with the particular magnet. Upon activation of the measurement circuitry, the portion of the perimeter may predominantly produce eddy currents in the tubular along a longitudinal axis of the tubular. The at least one receiver coil may comprise a center aligned with the particular magnet. The at least one conductive coil may comprise an array of coil loops wherein each coil loop of the array of coil loops has a magnetic dipole moment opposing each of the magnetic dipole moments of any adjacent coil loops of the array of coil loops. The array of coil loops may comprise a grid of rectangular coil loops proximate the first side of the magnet array. At least a first coil loop and a second coil loop of the array of coil loops may overlap such that mutual inductance between the first coil loop and the second coil loop is mitigated. The magnet array may comprise magnets arranged with a corresponding direction of magnetization of a first magnet oriented at a 45 degree angle with respect to a corresponding direction of magnetization of a second magnet.

Examples of the more important features of the disclosure have been summarized rather broadly in order that the detailed description thereof that follows may be better understood and in order that the contributions they represent to the art may be appreciated.

BRIEF DESCRIPTION OF THE DRAWINGS

For a detailed understanding of the present disclosure, reference should be made to the following detailed description of the embodiments, taken in conjunction with the accompanying drawings, in which like elements have been given like numerals, wherein:

FIGS. 5A-5D illustrate example magnet configurations for EMAT devices in accordance with embodiments of the present disclosure.

FIGS. 14A and 14B illustrate EMAT devices in accordance with embodiments of the present disclosure.

DETAILED DESCRIPTION

Figure 1:
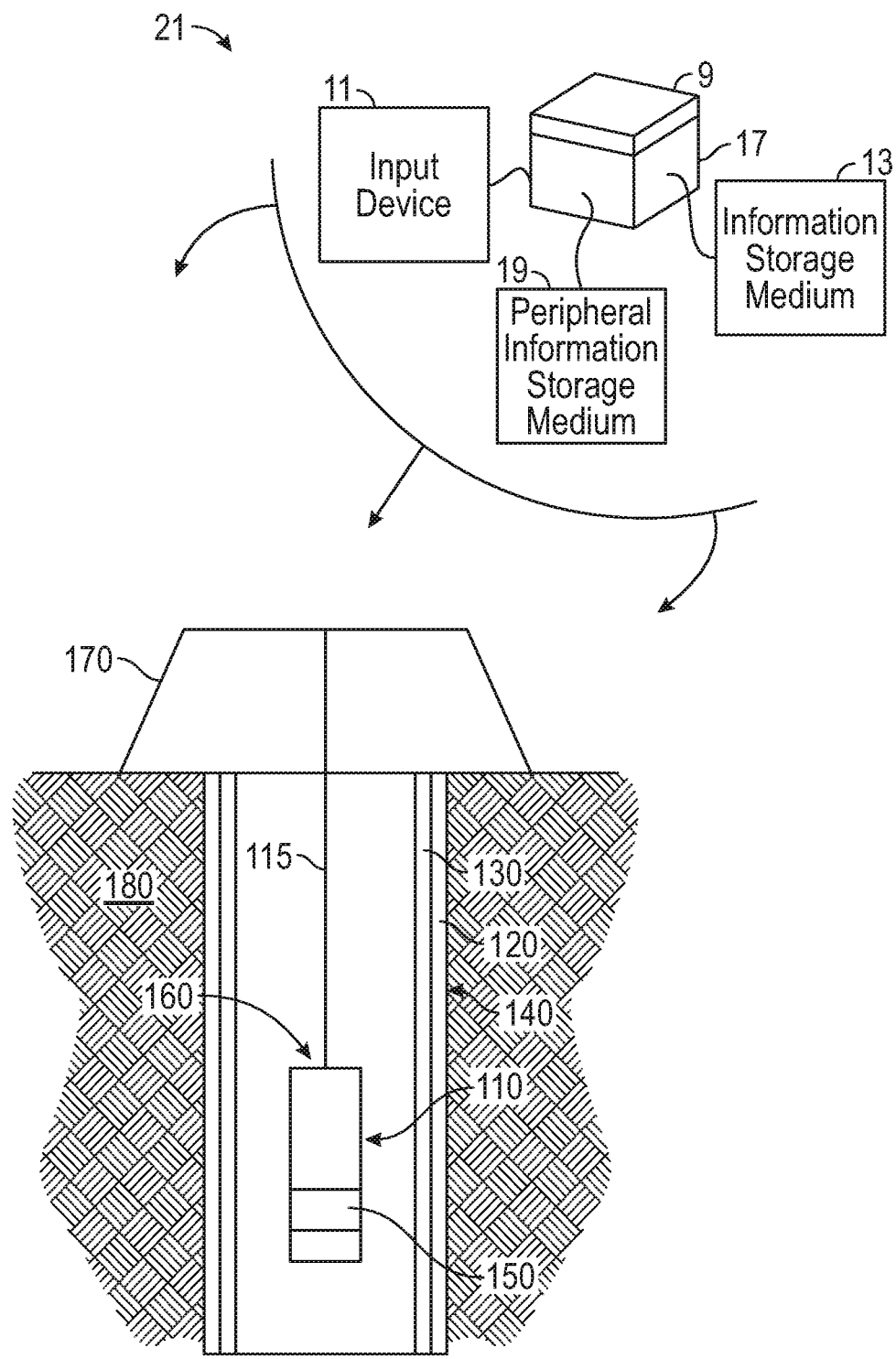
FIG. 1 illustrates an acoustic logging tool in accordance with embodiments of the present disclosure.

Aspects of the present disclosure relate to servicing boreholes with electric wireline tools and Logging While Drilling (LWD) tools. In one aspect, the present disclosure relates to estimating parameters of interest relating to the borehole, the casing, the formation, or fluids therein, such as, but not limited to, properties of the cement bond between casing and a wall of the borehole. Further aspects relate to improved performance of downhole EMAT sensors in relation to a variety of criteria.

EMATs are commonly employed in ultrasonic nondestructive testing (NDT) devices, which do not require contact or couplant, because the Lorentz force is directly generated within the material adjacent to the transducer. Due to this couplant-free feature, an EMAT is suitable for automated inspection in harsh surface environment, no matter hot or cold, wet or dry. The EMAT is also an ideal transducer to excite shear horizontal (SH), Lamb, and other guided waves in conductive materials. As an emerging ultrasonic testing (UT) technique, EMAT can be used for thickness measurement, flaw detection, surface characterization, and material property assessment.

The present disclosure is susceptible to embodiments of different forms. There are shown in the drawings, and herein will be described in detail, specific embodiments of the present disclosure with the understanding that the present disclosure is to be considered an exemplification of the principles of the disclosure, and is not intended to limit the disclosure to that illustrated and described herein. Indeed, as will become apparent, the teachings of the present disclosure can be utilized for a variety of well tools and in all phases of well construction and production. Accordingly, the embodiments discussed below are merely illustrative of the applications of the present disclosure.

In aspects of the disclosure an EMAT may be configured for couplant-free acoustic wave generation and reception using electromagnetic Lorentz force mechanisms. Unlike conventional EMATs which suffer from low transduction efficiency in comparison to piezoelectric transducers, aspects of the present disclosure include EMAT devices with enhanced transduction efficiency implemented using various aspects of the present disclosure. Particular embodiments may include Halbach arrays of magnets as disclosed herein. Improvements in coil alignment and design are also disclosed. In other aspects, coils of the EMAT may be switched to distinct configurations for transmitting and receiving. Synergistic increases in efficiency may be achieved thought combinations of these aspects.

The EMAT device may include a plurality of coils, and the measurement circuitry may be configured to be switched between a transmit mode and a receive mode, wherein, while in the transmit mode, the measurement circuitry forms a first circuit optimized for transmission with at least some of the plurality of coils; and while in the receive mode, the measurement circuitry forms a second circuit optimized for reception with a portion of the plurality of coils. In the transmit mode, the plurality of coils may comprise multiple coil layers electrically connected in parallel; and in the receive mode, the plurality of coils may comprise multiple coil layers electrically connected in series. At least a portion of the coil layers for each mode may include the same coils. That is, a subset of the coils on the device may be used in the transmit mode and another subset of coils on the device may be used in the receive mode, with the two subsets having overlap, or even being identical in some cases.

EMAT coil designs are configured to coordinate with specific EMAT magnet arrangements. Example horizontal shear wave (SH) EMATs are disclosed illustrating EMAT coil optimization. But techniques of the present disclosure are not limited to the configurations set forth, or to horizontal shear EMATs, or EMAT devices based on Lorentz forces. The present disclosure is applicable to EMATs of all types, including those using Lorentz force and magnetostriction mechanisms.

As discussed above, aspects of the present disclosure relate to use of EMAT devices, such as, for example, sensors, in downhole applications. One example application is producing and detecting acoustic forces within a wellbore casing to evaluate the integrity of the casing.

Wellbores often comprise casing set within the borehole, where the casing is bonded to the borehole wall by adding cement within the annulus formed between the outer diameter of the casing and the inner diameter of the borehole. The cement bond not only adheres to the casing within the wellbore, but also serves to isolate adjacent zones within an earth formation. Isolating adjacent zones can be important when one of the zones contains oil or gas and the other zone includes a non-hydrocarbon fluid such as water. Should the cement surrounding the casing be defective and fail to provide isolation of the adjacent zones, water or other undesirable fluid can migrate into the hydrocarbon producing zone thus diluting or contaminating the hydrocarbons within the producing zone, and increasing production costs, delaying production or inhibiting resource recovery.

Historically, to detect possible defective cement bonds, downhole tools were developed for analyzing the integrity of the cement bonding the casing to the wellbore. These downhole tools are lowered into the wellbore by wireline in combination with a pulley and typically include transducers disposed on their outer surface formed to be acoustically coupled to the fluid in the borehole. These transducers are generally capable of emitting acoustic waves into the casing and recording the amplitude of the acoustic waves as they travel, or propagate, across the casing. Characteristics of the cement bond, such as its efficacy, integrity and adherence to the casing, can be determined by analyzing characteristics of the acoustic wave such as attenuation. Typically the transducers are piezoelectric devices having a piezoelectric crystal that converts electrical energy into mechanical vibrations or oscillations transmitting acoustic wave to the casing. Piezoelectric devices typically couple to a casing through a coupling medium found in the wellbore, e.g., downhole fluids. However, lower density fluids such as gas or air and high viscosity fluids such as some drilling mud may not provide adequate coupling between a piezoelectric device and the casing. Furthermore, the presence of sludge, scale, or other like matter on the inner circumference of the casing can detrimentally affect the efficacy of a bond log acquired with a piezoelectric device. Another drawback faced when employing piezoelectric devices for use in bond logging operations involves the limitation of variant waveforms produced by these devices.

More recently, to address these drawbacks, EMAT devices have been employed downhole for use in cement bond evaluation (as well as other contexts). Electromagnetic phenomena generated by the EMAT device causes an acoustic excitation in the object. In a reciprocal use, an electric signal will be generated at the device as a result of the acoustic excitation.

FIG. 1 illustrates an acoustic logging tool in accordance with embodiments of the present disclosure. The tool 110 is configured to be conveyed in a borehole intersecting a formation 180. The borehole wall 140 is lined with casing 130 filled with a downhole fluid 160, such as, for example, drilling fluid. Cement 120 fills the annulus between the borehole wall 140 and the casing 130. In one illustrative embodiment, the tool 110 may contain a sensor unit 150, including, for example, one or more EMATs, including a magnet array and at least one sensor coil, configured for evaluation of the cement bond existing between the system of the casing 130, the borehole wall 140, and the cement 120 according to known techniques. For example, electronics in the tool 110, at the surface, and/or elsewhere in system 101 (e.g., at least one processor) may be configured to use acoustic measurements to derive information such as time or arrival, group velocity, frequency content, and damping, and to determine properties of the cement bond with this information using known techniques, such as, for example, analysis of casing resonance.

The system 101 may include a conventional derrick 170. A conveyance device (carrier 115) which may be rigid or non-rigid, may be configured to convey the downhole tool 110 into wellbore 140 in proximity to formation 180. The carrier 115 may be a drill string, coiled tubing, a slickline, an e-line, a wireline, etc. Downhole tool 110 may be coupled or combined with additional tools. Thus, depending on the configuration, the tool 110 may be used during drilling and/or after the wellbore (borehole) 140 has been formed. While a land system is shown, the teachings of the present disclosure may also be utilized in offshore or subsea applications. The carrier 115 may include embedded conductors for power and/or data for providing signal and/or power communication between the surface and downhole equipment. The carrier 115 may include a bottom hole assembly, which may include a drilling motor for rotating a drill bit.

General method embodiments may include conveying a carrier in the borehole, the carrier having disposed thereon an EMAT sensor device and making measurement with the EMAT sensor device in the borehole; and using the sensor measurements to estimate at least one parameter of interest.

Apparatus embodiments may include a sensor including an electromagnetic acoustic transducer (EMAT) device configured to be conveyed into the tubular. The EMAT device may include measurement circuitry comprising at least one conductive coil; and a magnet array comprising magnets arranged with a corresponding direction of magnetization of each magnet oriented according to a configuration producing a greater magnetic flux on a first side of the array than on a second side opposing the first side. The EMAT device may generate measurement information indicative of the tubular or a cement bond between the tubular and the formation. The information is indicative of a parameter of interest. The term "information" as used herein includes any form of information (analog, digital, EM, printed, etc.), and may include one or more of: raw data, processed data, and signals.

Methods may include estimating a parameter of interest from the information, evaluating the formation using the parameter of interest, and/or performing further borehole or formation operations in dependence upon the evaluation or the parameter of interest. In particular embodiments, a state of drilling operations, characteristics of the borehole or formation, or orientation of components of the downhole tool may be estimated using the parameter of interest, and then used in performing an operation as described above.

In one embodiment, electronics associated with sensors 40 may be configured to record and/or process the information obtained. Certain embodiments of the present disclosure may be implemented with a hardware environment 21 that includes an information processor 17, an information storage medium 13, an input device 11, processor memory 9, and may include peripheral information storage medium 19. The hardware environment may be in the well, at the rig, or at a remote location. Moreover, the several components of the hardware environment may be distributed among those locations. The input device 11 may be any data reader or user input device, such as data card reader, keyboard, USB port, etc. The information storage medium 13 stores information provided by the detectors. Information storage medium 13 may include any non-transitory computer-readable medium for standard computer information storage, such as a USB drive, memory stick, hard disk, removable RAM, EPROMs, EAROMs, flash memories and optical disks or other commonly used memory storage system known to one of ordinary skill in the art including Internet based storage. Information storage medium 13 stores a program that when executed causes information processor 17 to execute the disclosed method. Information storage medium 13 may also store the formation information provided by the user, or the formation information may be stored in a peripheral information storage medium 19, which may be any standard computer information storage device, such as a USB drive, memory stick, hard disk, removable RAM, or other commonly used memory storage system known to one of ordinary skill in the art including Internet based storage. Information processor 17 may be any form of computer or mathematical processing hardware, including Internet based hardware. When the program is loaded from information storage medium 13 into processor memory 9 (e.g. computer RAM), the program, when executed, causes information processor 17 to retrieve detector information from either information storage medium 13 or peripheral information storage medium 19 and process the information to estimate a parameter of interest. Information processor 17 may be located on the surface or downhole.

The term "information" as used herein includes any form of information (analog, digital, EM, printed, etc.). As used herein, a processor is any information processing device that transmits, receives, manipulates, converts, calculates, modulates, transposes, carries, stores, or otherwise utilizes information. In several non-limiting aspects of the disclosure, an information processing device includes a computer that executes programmed instructions for performing various methods. These instructions may provide for equipment operation, control, data collection and analysis and other functions in addition to the functions described in this disclosure. The processor may execute instructions stored in computer memory accessible to the processor, or may employ logic implemented as field-programmable gate arrays ('FPGAs'), application-specific integrated circuits ('ASICs'), other combinatorial or sequential logic hardware, and so on. In one embodiment, circuitry associated with the sensor 150 (described in further detail below with respect to FIGS. 8A-8D) may be configured to take measurements at a plurality of locations as the tool moves along the longitudinal axis of the borehole ('axially') using sensor 150.

In other embodiments, circuitry may be located elsewhere (e.g., at the surface, or remotely). To perform the treatments during a single trip, the tool may use a high bandwidth transmission to transmit the information acquired by sensor 150 to the surface for analysis. For instance, a communication line for transmitting the acquired information may be an optical fiber, a metal conductor, or any other suitable signal conducting medium. It should be appreciated that the use of a "high bandwidth" communication line may allow surface personnel to monitor and control operations in "substantially real-time."

One point of novelty of the system illustrated in FIG. 1 is that the at least one processor may be configured to perform certain methods (discussed below) that are not in the prior art. A surface control system or downhole control system may be configured to control the tool described above and any incorporated sensors and to estimate a parameter of interest according to methods described herein.

Mathematical models, look-up tables, or other models representing relationships between the signals and the values of the formation properties may be used to characterize operations in the formation or the formation itself, optimize one or more operational parameters of a production or development, and so on. The system may carry out these actions through notifications, advice, and/or intelligent control.

In embodiments, the system may be configured to perform a number optimization procedures including the transmission and reception of a pre-defined optimum frequency spectrum and time-domain sequence before or during the measurement operation (e.g., surveying the surrounding media including, for example, the casing and cement layers). The resulting exploratory measurements can be used to automatically optimize measurements with respect to one or more criteria including, for example, time, quality, reliability, energy consumed, operational errors, and the like. An automation algorithm with look-up tables, algorithm optimization, fuzzy logic or neural networks, global inversions optimization techniques or a combination of these techniques may be used to automate the operation of the downhole tool.

Figure 2A:
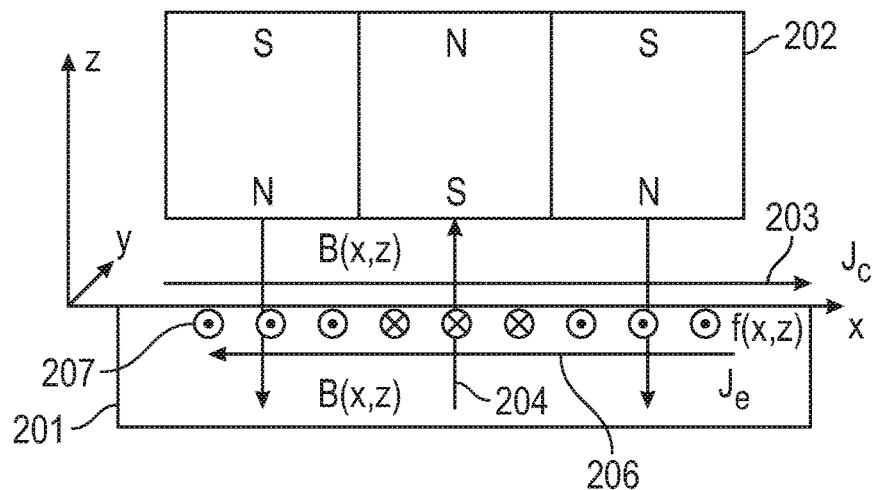
FIGS. 2A-2C illustrate basic principles for shear wave excitation based on Lorenz force in accordance to embodiments of the present disclosure.
Figure 2B:
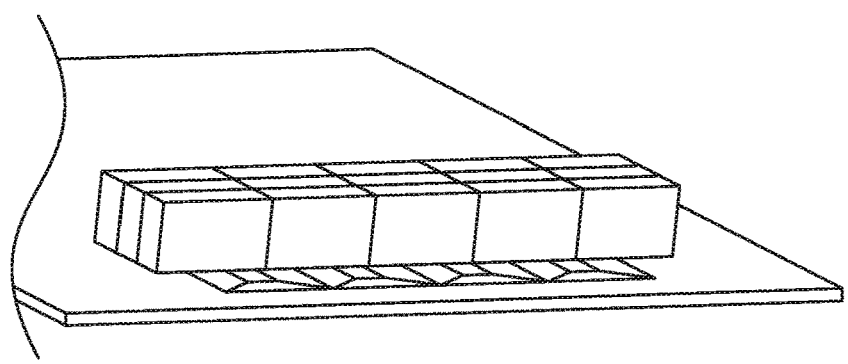
Figure 2C:
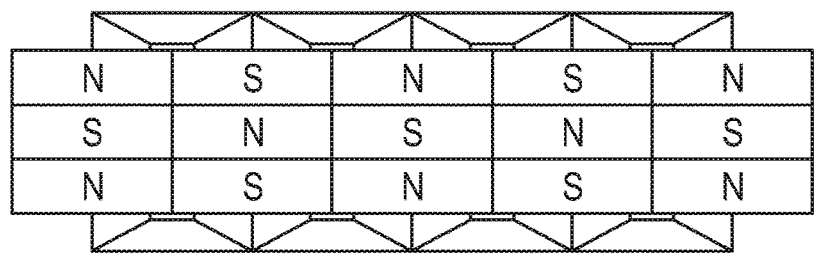
Figure 3A:
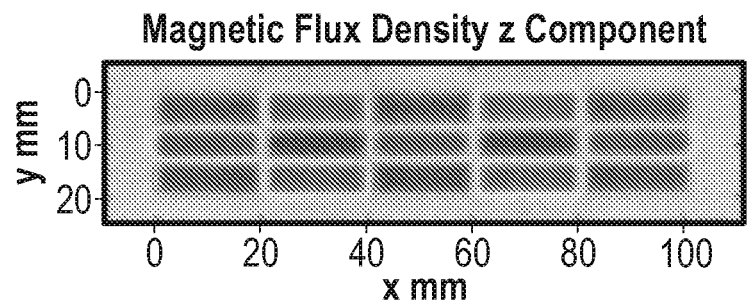
FIGS. 3A-3C show simulation results at the surface of a steel plate illustrating electromagnetic phenomena resulting from the shear wave excitation.
Figure 3B:
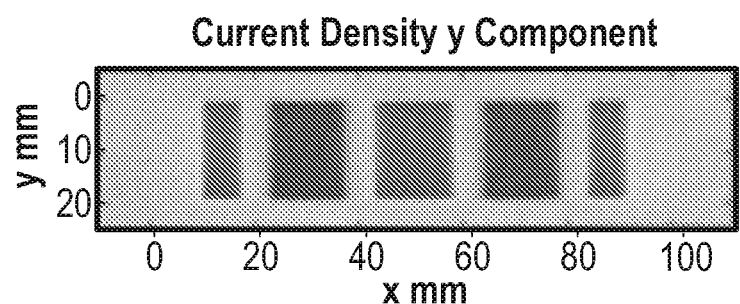
Figure 3C:
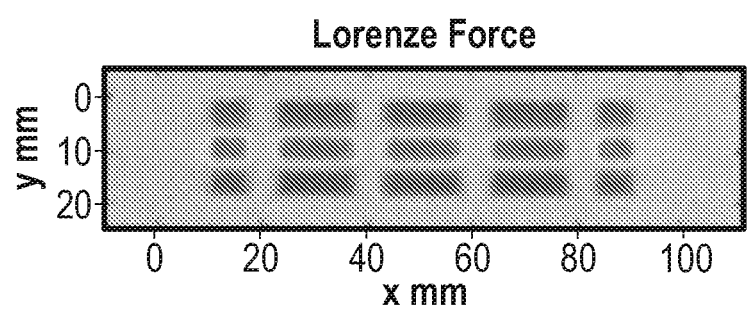

FIGS. 2A-2C illustrate basic principles for shear wave excitation based on Lorenz force in accordance to embodiments of the present disclosure. FIGS. 3A-3C show simulation results at the surface of a steel plate illustrating electromagnetic phenomena resulting from the shear wave excitation. FIG. 3A shows distribution of magnetic flux density in the z direction ($B_z$). FIG. 3B shows distribution of eddy current density in y direction ($J_y$). FIG. 3C shows distribution of Lorenz force in x direction ($F_x$).

FIG. 2A shows basic geometry for the shear wave (SH) EMAT excitation based on a Lorenz force. There is an array of alternating permanent magnets 202 that produces constant magnetic field B, indicated by 204, across a metal 201. An alternating current Jc, indicated by 203, flows in the x-direction in a coil located between magnets 202 and a metal 201. This alternating current induces in a coils' proximate volume of metal 201 an eddy current Je, indicated by 206, that flows in the opposite direction. The mutual interaction of the bias magnetic field B and eddy current Je generates Lorentz force f, indicated by 207 (in the direction perpendicular to the picture plane). In turn, this volume force produces a displacement in the metal. The three equations below represent respectively the acoustic amplitude, the receiver signal ($V_r$) and the transducer efficiency defined as receive signal per unit current in the transmit wire ($I_{exc}$):

$$u \propto \frac{B_0 \cdot I_{exc}}{G} \cdot K_t, \text{ for } \delta \ll \lambda_a, \quad (1)$$

$$V_r \propto u \cdot B_0 \cdot K_r, \quad (2)$$

$$\frac{V_r}{I_{exc}} \propto B_0^2 \cdot K_r \cdot K_t. \quad (3)$$

Here, u is the acoustic amplitude, $B_0$ is the static magnetic field, $I_{exc}$ is the excitation coil current which magnetic field induces eddy currents in the metal, G is the shear modulus, $K_r$ and $K_t$ are the receiver and transmitter sensitivity functions (defined based on reciprocity principle as the magnetic field generated magnetic field per unit current), $\delta = \sqrt{2/(\omega\sigma\mu)}$ is the electromagnetic skin depth in the object with conductivity σ and absolute magnetic permeability μ at excitation frequency ω, and $\lambda_a$ is the wavelength of the acoustic excitation.

FIGS. 2B & 2C show a device schematic illustrating principles of the shear wave excitation based on Lorenz force. An array of permanent alternative polarized magnets produces the alternative magnetic flux density in the z direction ($B_z$). When an alternating current with a central frequency $f$ is applied to the EMAT's coil circuit beneath the magnets, eddy currents will be induced within the skin depth of the adjacent conductive plate. The y component of eddy current density ($J_y$) measured at the surface of the steel plate is also shown. Lorenz force can be calculated using $$F = J \times B = \begin{bmatrix} 0 \\ J_y \\ 0 \end{bmatrix} \times \begin{bmatrix} B_x \\ B_y \\ B_z \end{bmatrix} = \begin{bmatrix} J_y B_z \\ 0 \\ -J_y B_x \end{bmatrix} \cong \begin{bmatrix} J_y B_z \\ 0 \\ 0 \end{bmatrix}, \quad (4)$$

because, in this case, the component $B_x$ of the bias magnetic field is negligible in comparison to $B_z$. Therefore, for SH waves, we obtain Lorentz force in x direction ($F_x$), $$F_x = J_y B_z \quad (5).$$

Thus, the SH wave will be generated in the plate or pipe with the particle displacement at x direction and direction of propagation in y direction, with the initial wave pattern illustrated by FIGS. 3A-3C. The central frequency of the excited SH waves is determined by the frequency of the AC currents, while the central wavelength of the SH waves is governed by the width of the magnets in the y direction (here, it is twice the width in y direction). Since guided wave excitation is strongly affected by mode selection, it is possible to design the SH EMAT device with a particular central wavelength by changing the size of the magnets in dependence upon dispersion curves of the plate or pipe to be measured; the driving frequency can be swept to excite the particular SH modes under interest. In other embodiments, Lamb waves or other guided waves may be generated in addition to (or in the alternative to) shear waves.

Figure 4A:
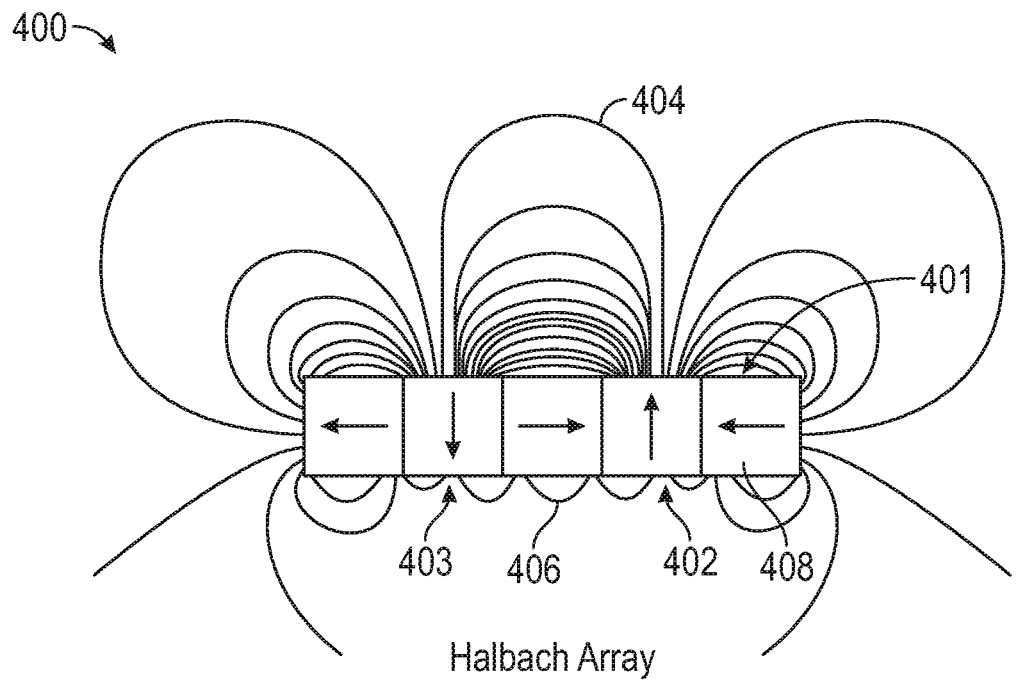
FIGS. 4A & 4B show a schematic diagram illustrating differences in patterns of magnetization between an example EMAT device of the present disclosure and a conventional device.
Figure 4B:
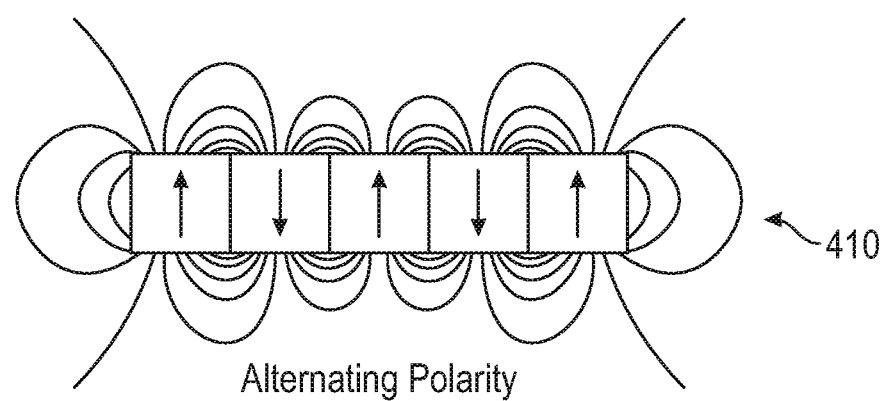

FIGS. 4A & 4B show a schematic diagram illustrating differences in patterns of magnetization between an example EMAT device of the present disclosure and a conventional device. FIG. 4A shows a schematic diagram of an example EMAT device 400 of the present disclosure, which employs a linear Halbach array 402 of magnets—that is, an array of permanent magnets in a linear Halbach configuration. Arrows point in a direction of magnetization for each magnet. A Halbach array is an arrangement of permanent magnets 408 that augments the magnetic field 404 on one side 401 (e.g. the sensing side) of the array 402 while cancelling the field 406 to substantially zero on the opposing side 403 by employing a spatially rotating pattern of magnetization. FIG. 4B illustrates a conventional array 410 of alternating polarity. It is apparent that magnetic flux is substantially greater on the sensing side of the array for the Halbach array 402 than for the conventional array 410, thereby amplifying the waves in the tubular.

FIGS. 5A-5D illustrate example magnet configurations for EMAT devices in accordance with embodiments of the present disclosure. FIG. 5A shows a 15 magnet conventional magnet array 501. FIG. 5B shows a 25 magnet Halbach array 511. Array 511 comprises five columns, wherein each column is an array of magnets in a linear Halbach array configuration. FIG. 5C shows a 45 magnet modified Halbach array 521. FIG. 5D shows another 45 magnet Halbach array 531. Arrays 521 and 531 each comprise rows of linear Halbach arrays with auxiliary magnet arrays between the linear Halbach arrays.

Figure 6A:
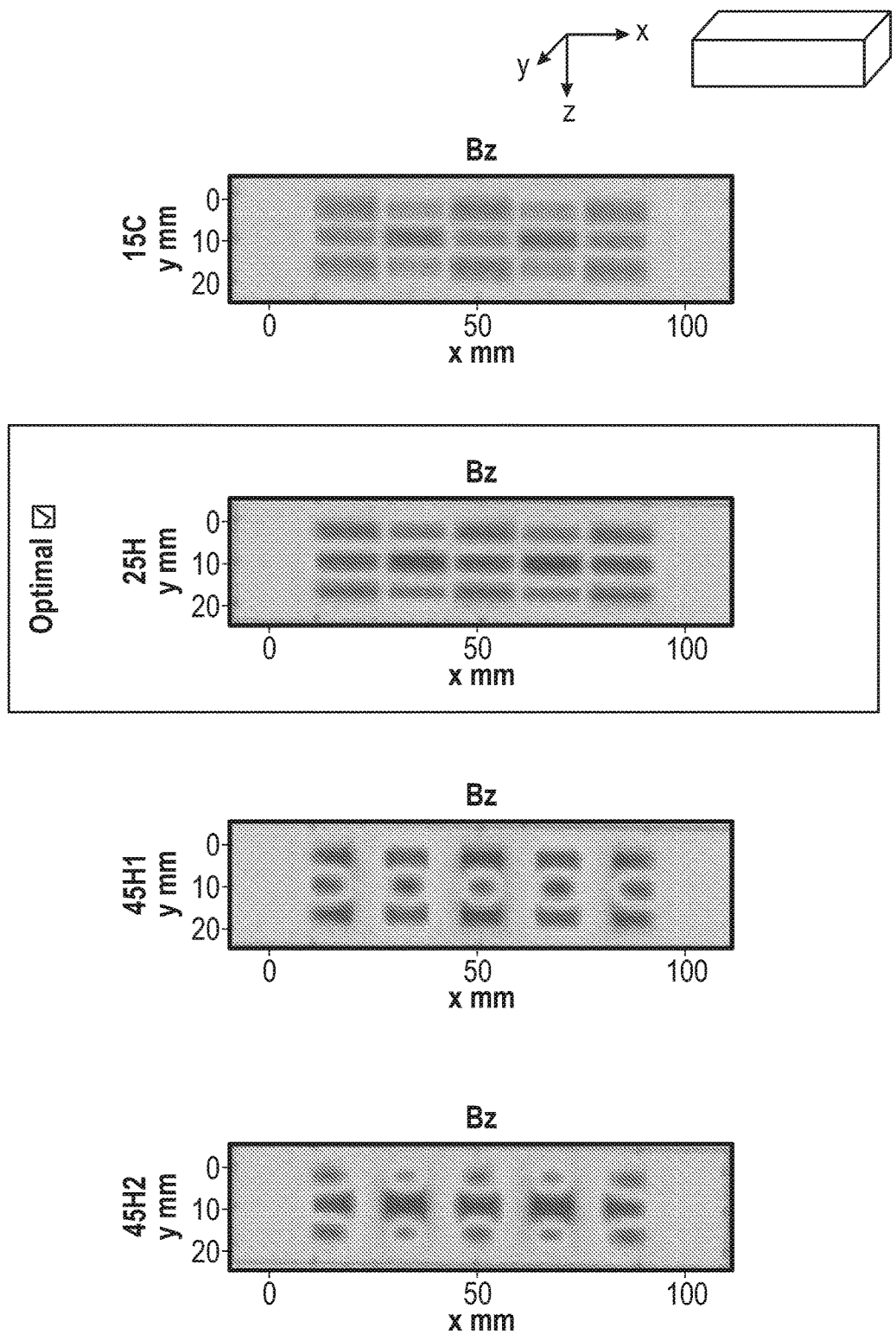
FIGS. 6A-6D show simulation results from a three-dimensional (3D) SH EMAT finite element model illustrating differences in electromagnetic phenomena resulting each of the arrays.
Figure 6B:
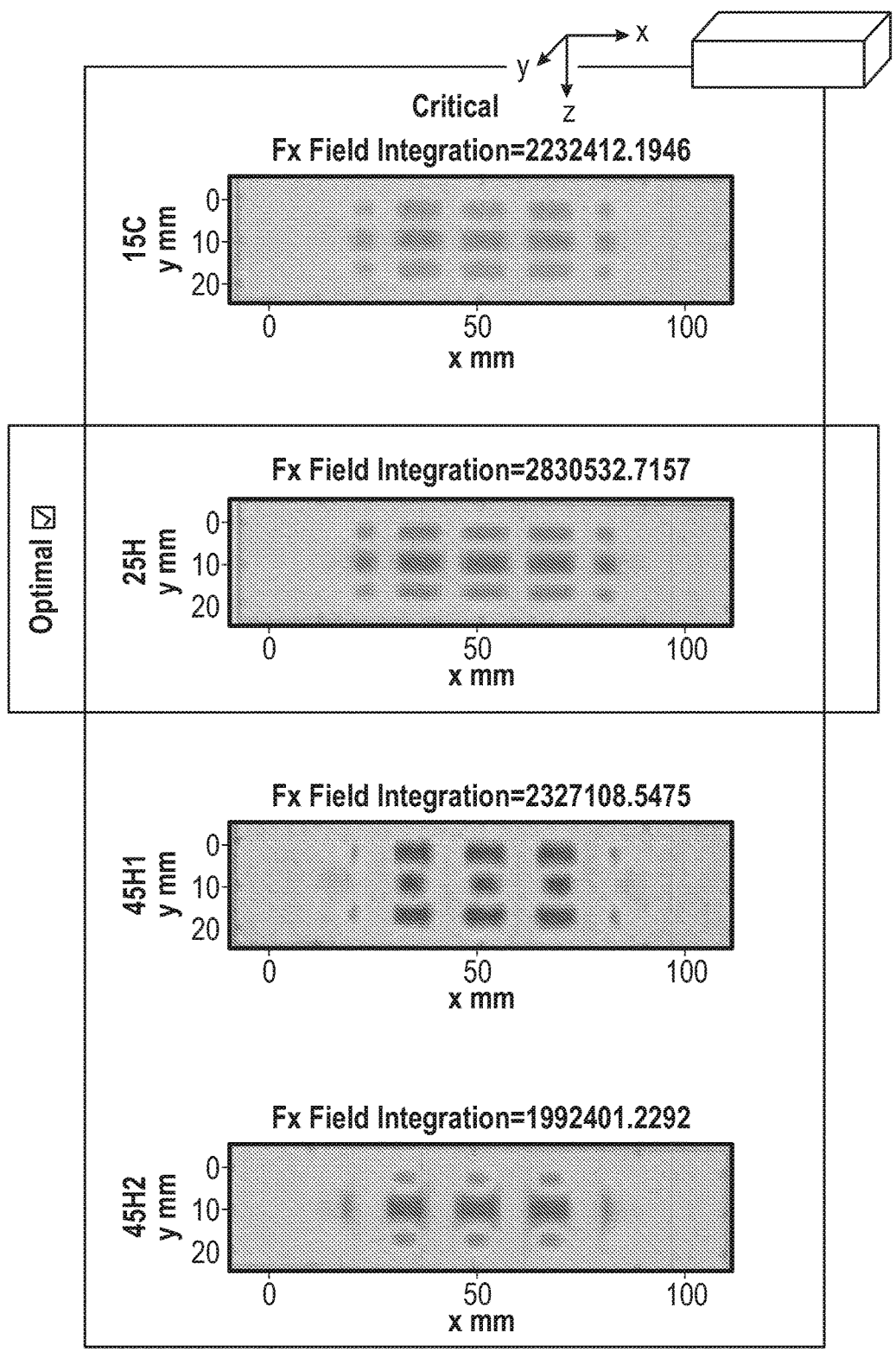
Figure 6C:
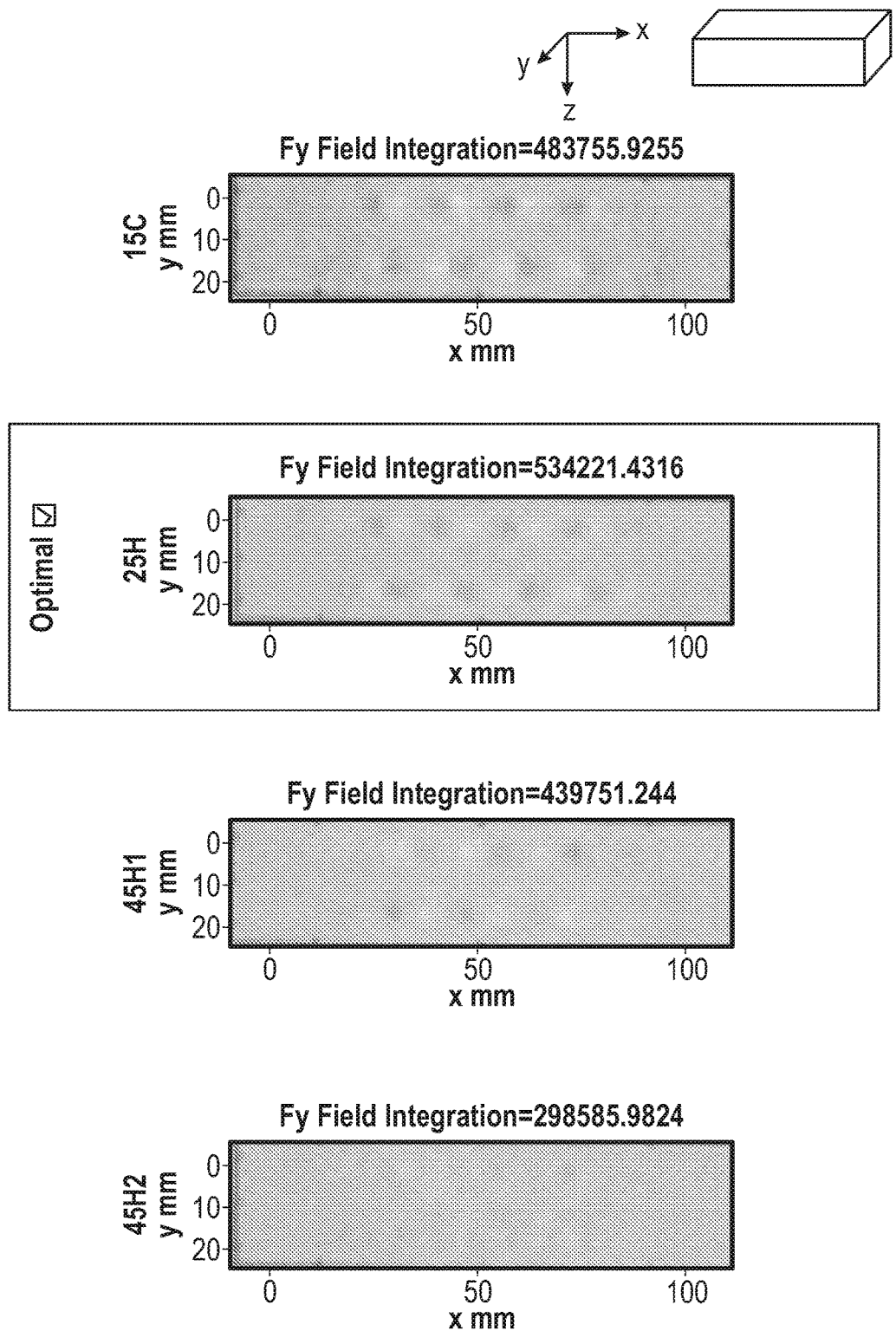
Figure 6D:
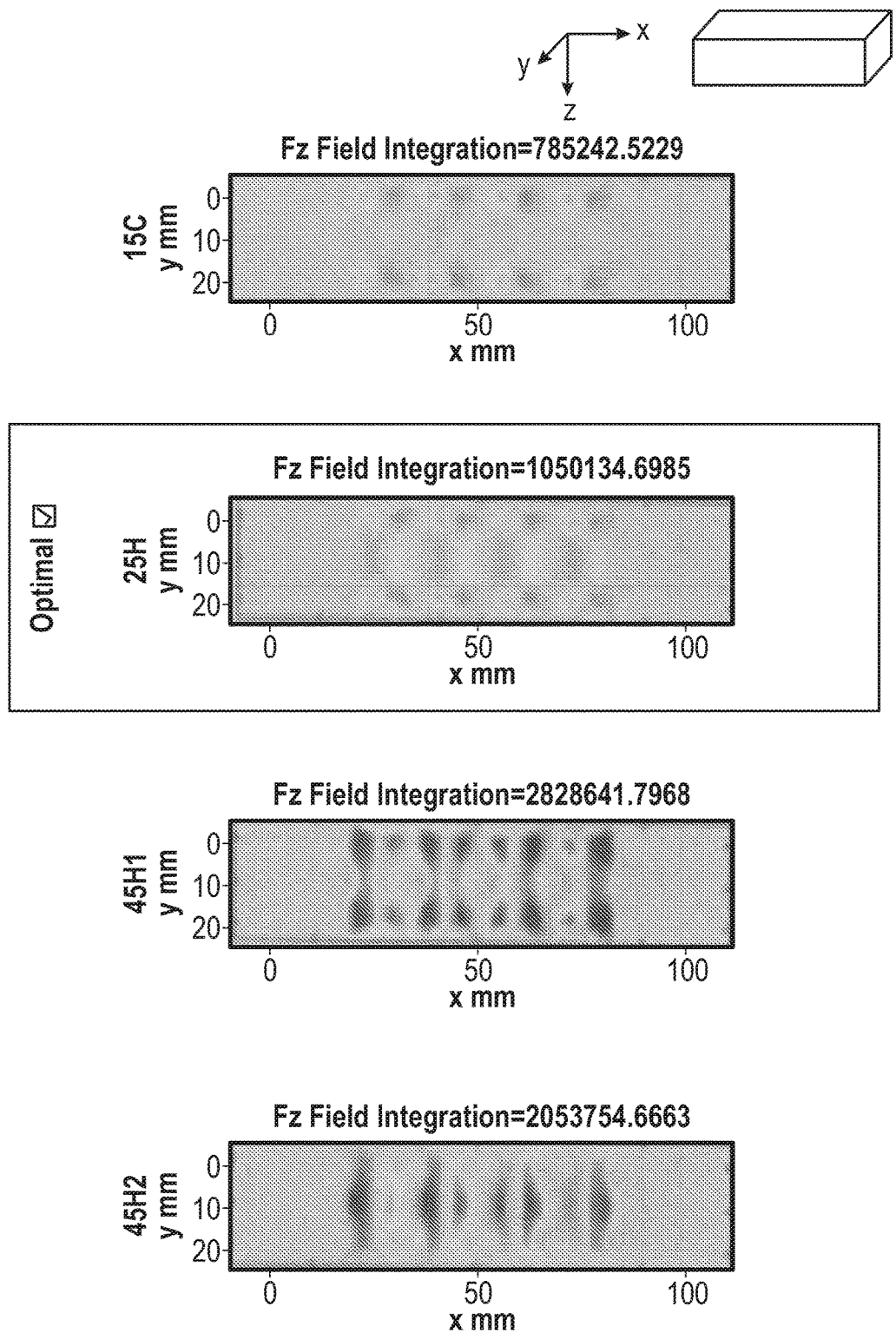

FIGS. 6A-6D show simulation results from a three-dimensional (3D) SH EMAT finite element model illustrating differences in electromagnetic phenomena resulting each of the arrays 501, 511, 521 and 531. FIG. 6A shows distribution of magnetic flux density in the z direction ($B_z$). FIG. 6B shows distribution of Lorenz force in x direction ($F_x$). FIG. 6C shows distribution of Lorenz force in y direction ($F_y$). FIG. 6D shows distribution of Lorenz force in z direction ($F_z$).

Array 511 has a $B_z$ distribution most similar to conventional array 501, while the magnitude of array 511 is obviously stronger. The $F_x$ distribution, which generates the SH wave in the plate, is also beneficial. The area integration of the $F_x$ for 511 is the strongest among the examples shown. Array 511 is also lower in energy for F. The $F_z$ for 521 and 531 have relatively high energy patterns in comparison, creating additional normal force to the plate. It is beneficial to suppress the $F_z$.

Experimental results conducted on a 0.512" aluminum plate validate the simulation results. A magnet and coil separable SH EMAT was used as a receiver (for signals responsive to a transmitter), with both the 501 array and the 511 array used as the receiver, keeping all other conditions the same. Two different excitation frequencies and number of cycles were selected to generate SH0, and SH1 dominated modes generated in the plate.

Figure 7B:
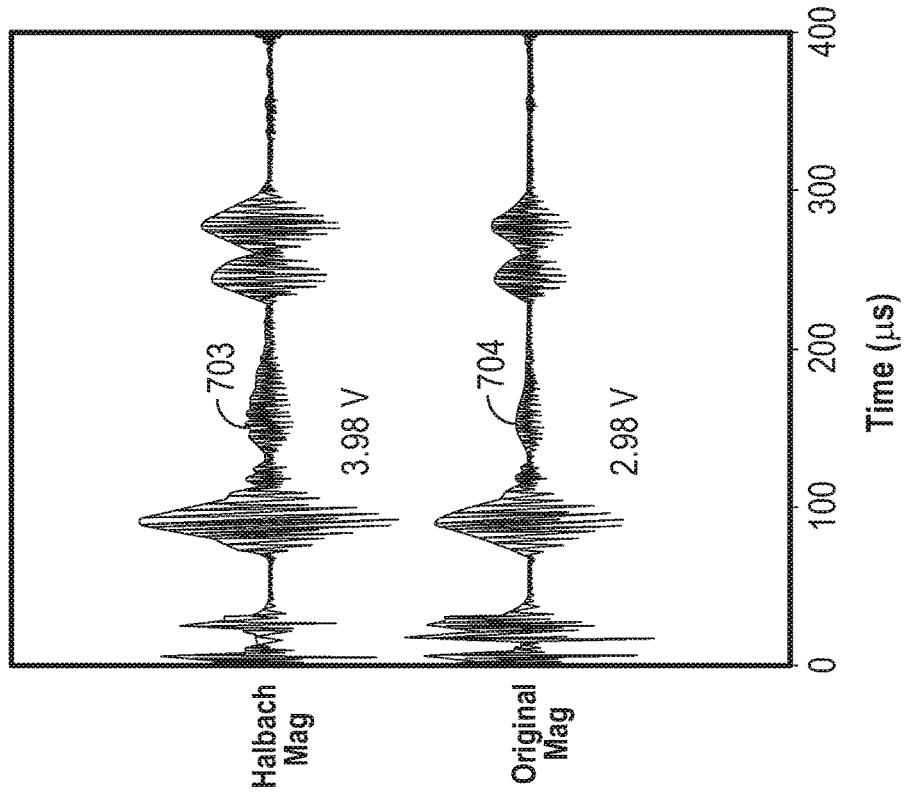
FIGS. 7A and 7B illustrate signal differences between EMAT devices using a conventional array and a Halbach array in accordance with embodiments of the present disclosure.
Figure 7A:
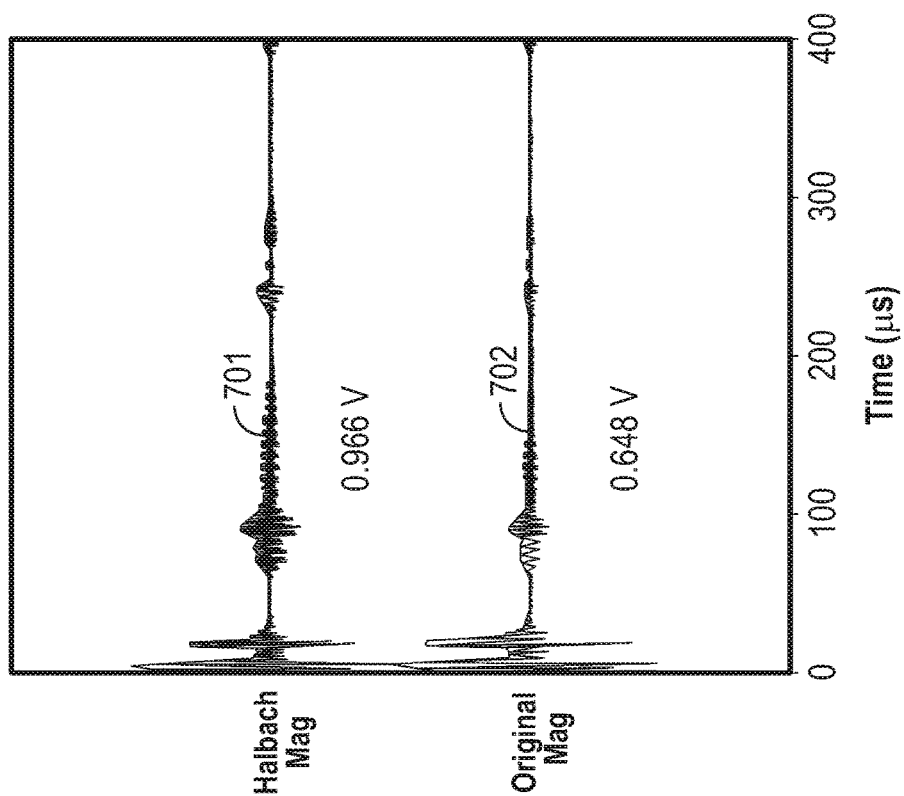

FIGS. 7A and 7B illustrate signal differences between EMAT devices using a conventional array and a Halbach array in accordance with embodiments of the present disclosure. FIG. 7A shows a curve 702 representing the signal response for the conventional array and a curve 701 representing the signal response for the Halbach array (511). Both signals represent one cycle of excitation of an SH0 wave mode at 150 kHz. The Halbach array device had a 3.46 dB gain from the conventional response under these conditions. FIG. 7B shows a curve 704 representing the signal response for the conventional array and a curve 703 representing the signal response for the Halbach array (511). Both signals represent five cycles of excitation of an SH1 wave mode at 250 kHz. The Halbach array device had a 2.51 dB gain from the conventional response under these conditions. Transmitter gain is expected to show similar behavior. Thus a total gain of 6.92 dB for SH0 and 5.02 dB for SH1 could be expected.

Single-coil configurations are traditionally used for both transmitter and receiver of an EMAT device. However, there's a general conflict for EMAT coil design. For the transmitter side, it is desirable to minimize the inductance of the coil in order to maximize the output currents. For the receiver side, it is desirable to maximize the inductance of the coil to have higher electrical voltage potential induced from eddy currents. Aspects of the present disclosure enable increased EMAT transduction efficiency by providing separate EMAT coil systems optimized for transmitter and receiver.

Figure 8A:
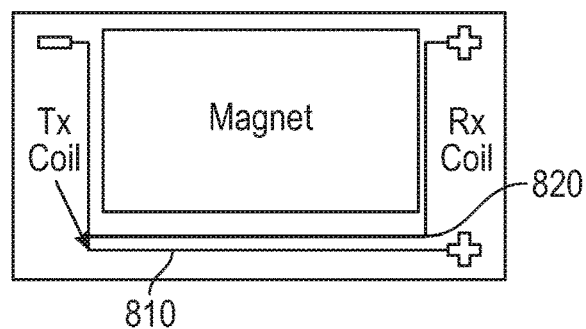
FIG. 8A illustrates an EMAT assembly with a multilayer coil configuration in accordance with embodiments of the present disclosure.

FIG. 8A illustrates an EMAT assembly with a multilayer coil configuration in accordance with embodiments of the present disclosure. The EMAT device includes a plurality of coils arranged as a multilayer coil assembly. The multilayer coil assembly includes separate sets of coils for transmitting and for receiving. Thus, the EMAT device comprises at least one transmitter coil and at least one receiver coil electrically non-identical to the at least one transmitter coil. The measurement circuitry may be configured to be switched between a transmit mode and a receive mode. While in the transmit mode, the measurement circuitry forms a first circuit optimized for transmission with at least some of the plurality of coils. While in the receive mode, the measurement circuitry forms a second circuit optimized for reception with a portion of the plurality of coils.

Referring to FIG. 8A, coil set 810 is optimized for transmitting, and coil set 820 is optimized for receiving. Assuming that a single coil layer has the electrical inductance L, for a transmitting coil set, the N layers of coils are connected in parallel, so that the inductance of the whole coil drops to R/L. For the receiving coil set, the N layers of coils are connected in series so that the inductance of the coil assembly increases approximately to N*L. Ideally, a gain of $N^2$ may be realized. Thus, an inductance of the at least one transmitter coil may be lower than an inductance of the at least one receiver coil. The at least one transmitter coil may include multiple coil layers electrically connected in parallel.

Each coil layer may have two connectors ("+" and "−") which are fed into a microprocessor. The EMAT transducer may be switchable from transmitter to receiver by selection of the feed from the 2N connectors from a microprocessor "transmitting stage"/in parallel to "receiving stage"/in series, or vice versa. The number of coil layers used for each of receiving and transmitting (and thus the total number of coils) may be optimized to maximize the gain while taking into account magnet liftoff effects. Thus, receiving coils in particular embodiments may be configured to increase a signal-to-noise ratio and a measurement dynamic range for received signals.

Figure 8B:
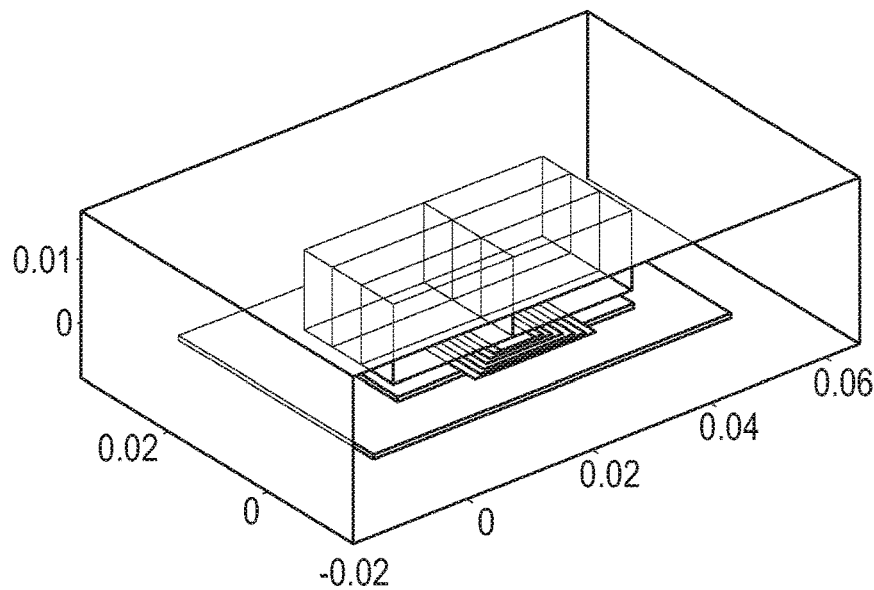
FIG. 8B illustrates a 3D Simplified Finite Element Analysis (FEA) model.
Figure 8C:
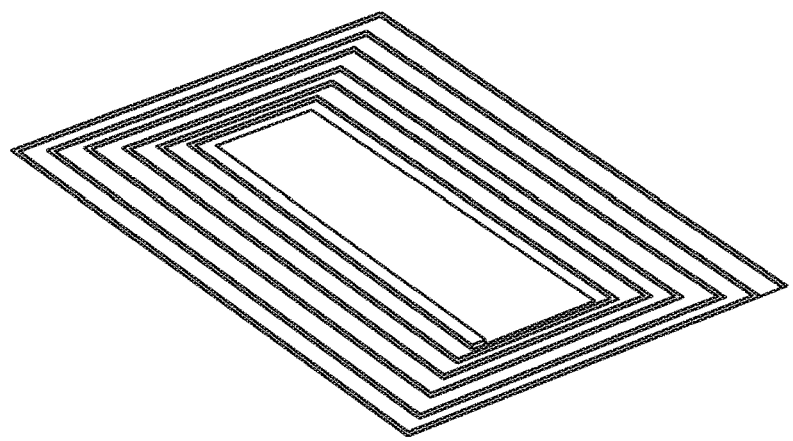
FIGS. 8C-8F illustrate different coil configurations for use in EMAT devices in accordance with embodiments of the present disclosure.
Figure 8D:
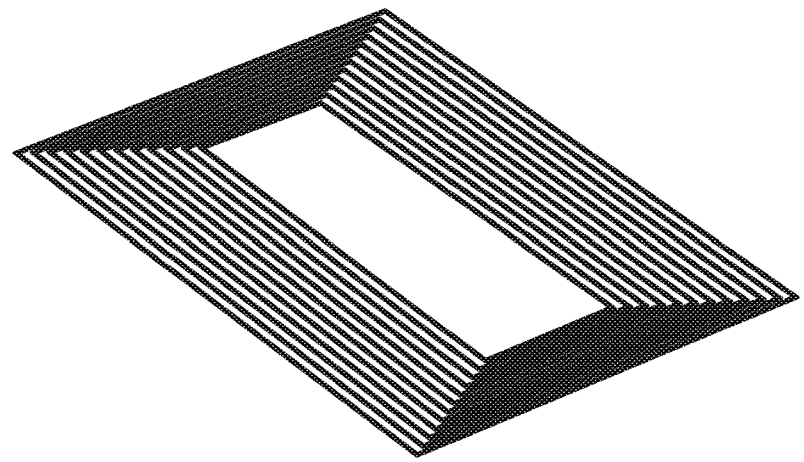
Figure 8E:
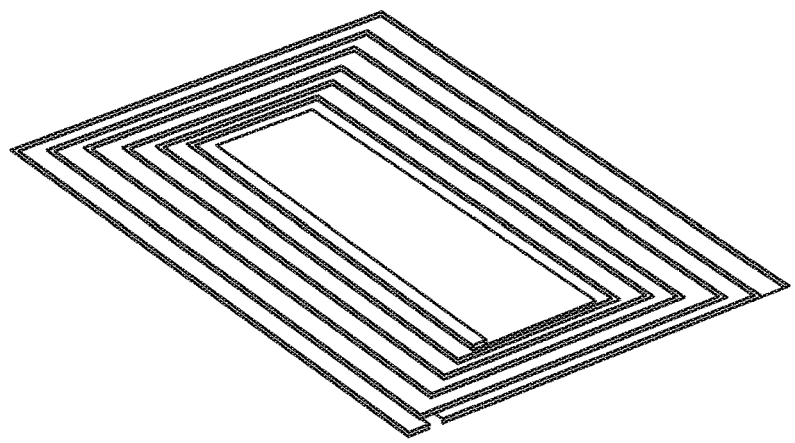
Figure 8F:
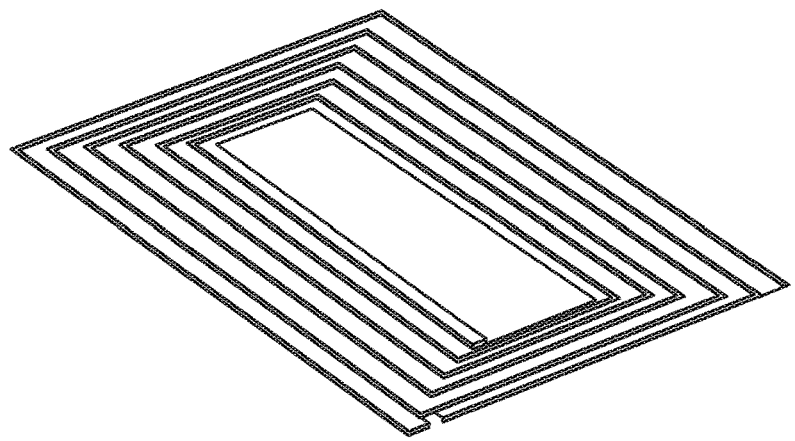

FIG. 8B illustrates a 3D Simplified Finite Element Analysis (FEA) model. The model consists of a 2 by 3 alternative magnet array and a 2 mm thick steel plate with 4 different coil configurations to be put in. FIGS. 8C-8F illustrate different coil configurations for use in EMAT devices in accordance with embodiments of the present disclosure. FIG. 8C shows a single layer coil. FIG. 8D shows a single layer coil with double the number of turns. FIG. 8E shows a double layer coil connected in series. FIG. 8F shows a double layer coil connected in parallel.

Each of the four coil configurations were simulated with a transmitting model and a receiving model. In the transmitting model, the same AC voltage potential was fed into the coil and the Lorentz force area integration was compared in the x direction. For the receiving model, the same induced currents were used in the steel plate while comparing the voltage potential of the coils.

Figure 9A:
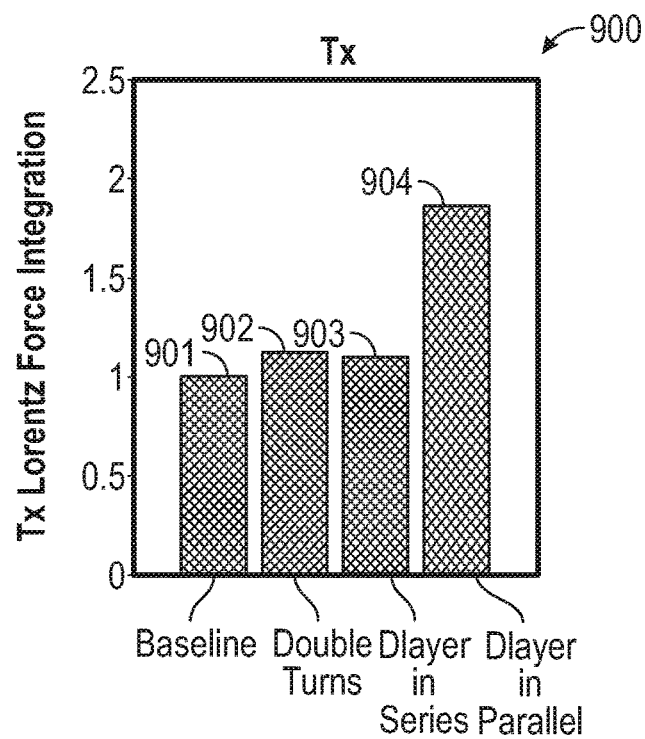
FIGS. 9A & 9B are graphical depictions illustrating simulation results normalized to the baseline single layer coil configuration.
Figure 9B:
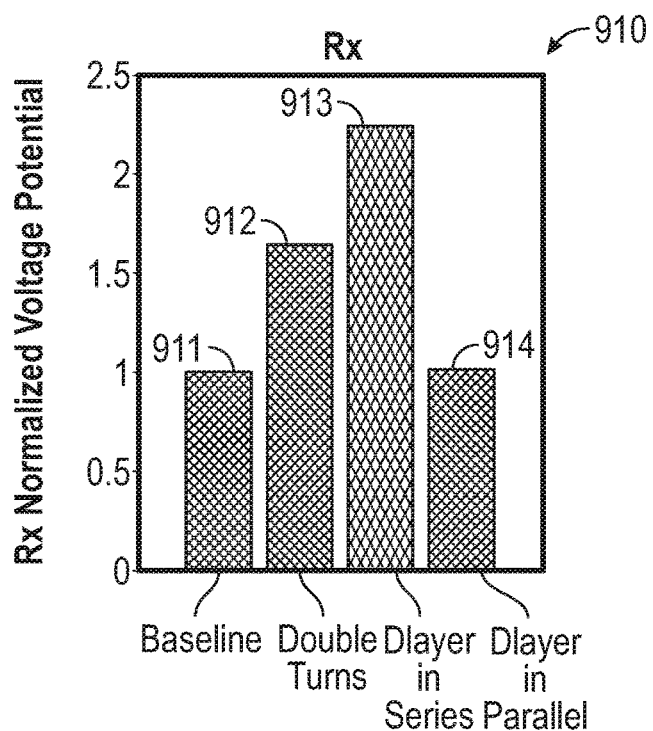

FIGS. 9A & 9B are graphical depictions 900 and 910 illustrating simulation results normalized to the baseline single layer coil configuration 901 and 911 for transmitting and receiving, respectively. Referring to FIG. 9A, for transmitting, the simulation results represent double turns 902, double layer in series 903, and double layer in parallel 904. Only the double layer in parallel has a significant gain, which amplifies the signal by 5.34 dB. Referring to FIG. 9B, for receiving, the simulation results represent double turns 912, double layer in series 913, and double layer in parallel 914. The double turns coil configuration will strengthen the signal by 4.24 dB, but the double layer in series configuration will amplify the signal by 6.97 dB. These results verify the following assumptions: an increase in the number of turns of coil will only benefit the receiving mode; multiple layers of coils in series will only benefit the receiving mode; multiple layers of coils in parallel will only benefit the transmitting mode.

Figure 9C:
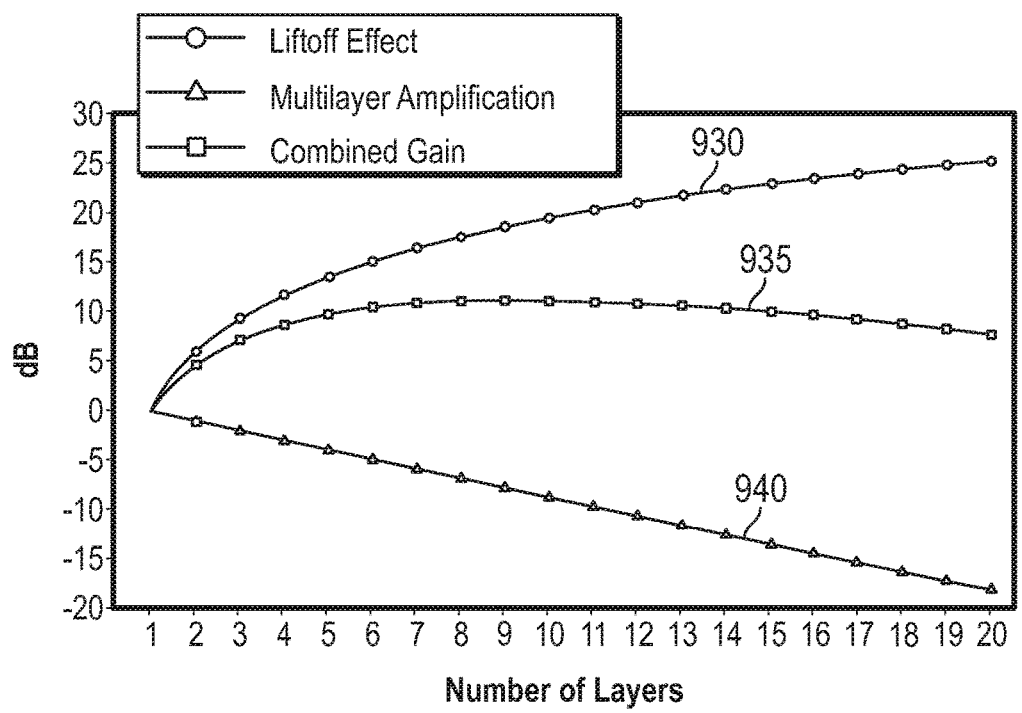
FIG. 9C illustrates results of an additional simulation.

FIG. 9C illustrates results of an additional simulation related to liftoff effects. In the simulation, the distance between magnets and steel plate were iteratively modified. A typical single coil layer thickness measured at 0.15 mm was used for the simulation. As shown in curve 940, a 0.94 dB per coil layer drop occurs due to liftoff associated with thickness increase from additional coils. It was assumed that N coil layers will in average amplify the signal by N times for a transmitter or receiver. When the multilayer amplification 930 is combined with liftoff effect, the combined gain 935 increases very fast at the beginning but reaches a maximum of 11.55 dB combined gain at 9 layers. Using separate coil configurations for transmitting and receiving, a maximum 23 dB gain may be achieved.

Figure 10A:
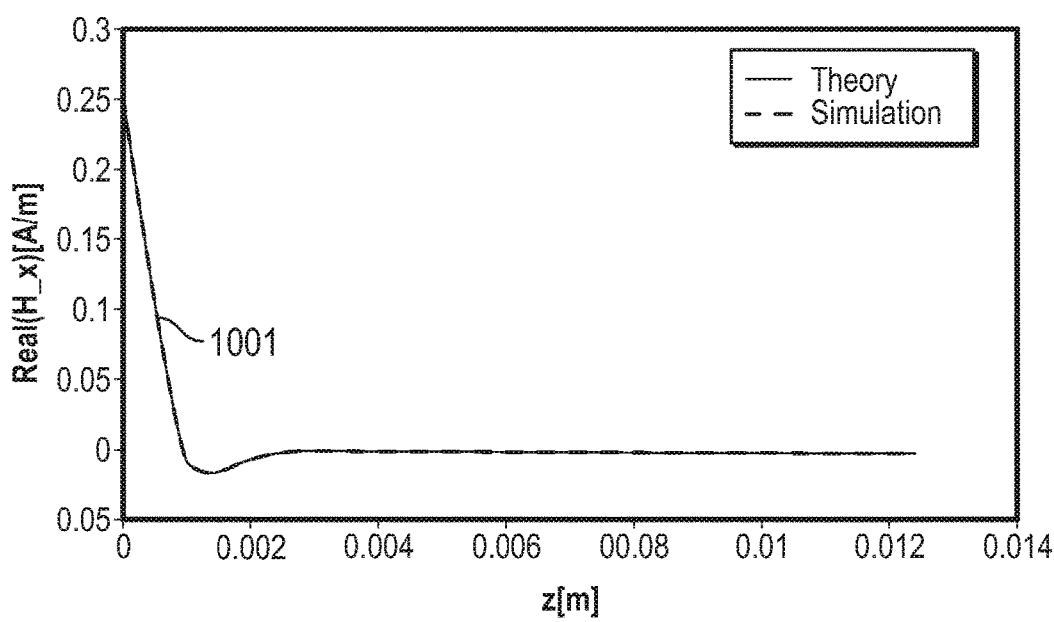
FIGS. 10A-10C illustrate effects of a location of a target.
Figure 10B:
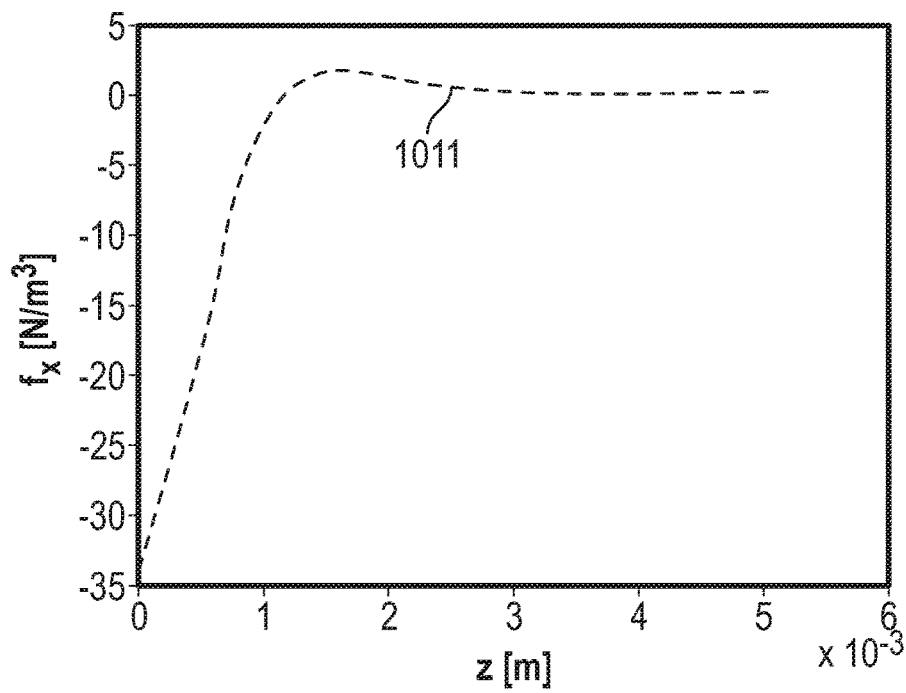
Figure 10C:
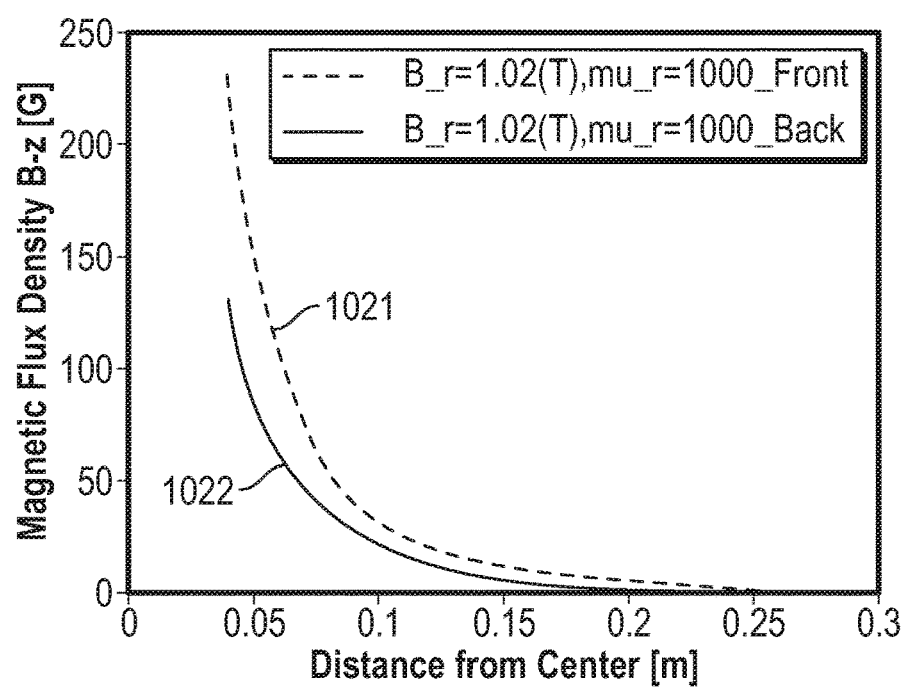

FIGS. 10A-10C illustrate effects of a location of a target with respect to the coil on EMAT effectiveness. FIG. 10A shows a curve 1001 representing the strength of the magnetic field produced by a coil with respect to a distance z from the plane of the coil. FIG. 10B shows a curve 1011 representing a Lorentz force generated by the coil with respect to a distance z from the plane of the coil. It is apparent from FIGS. 10A and 10B that the magnetic field generated by a coil is quite sensitive to the distance from the front of magnet. The associated Lorentz force becomes negligible after few millimeters. FIG. 10C compares the magnetic flux density at the back of the magnet to that of the front of the magnet. Curve 1021 represents the magnetic flux density at the front of the magnet with respect to distance from the center. Curve 1022 represents the magnetic flux density at the back of the magnet with respect to distance from the center.

Figure 11A:
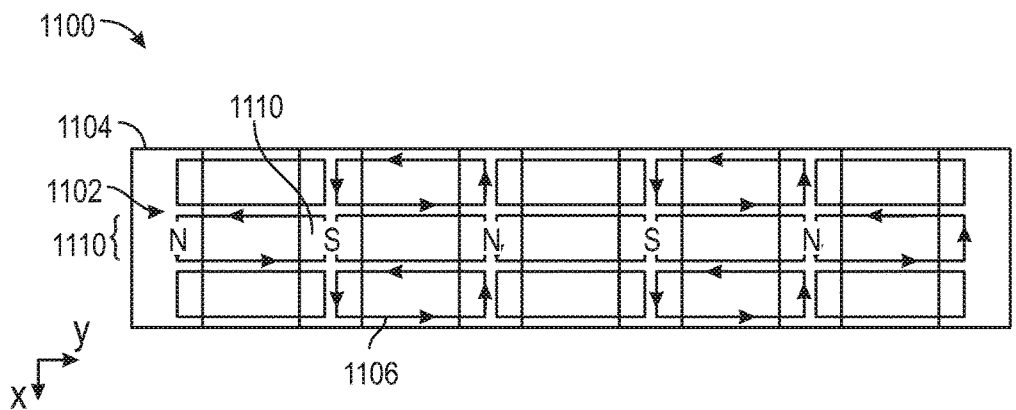
FIGS. 11A & 11B show schematic views illustrating coil alignment of an example EMAT device in accordance with embodiments of the present disclosure.
Figure 11B:
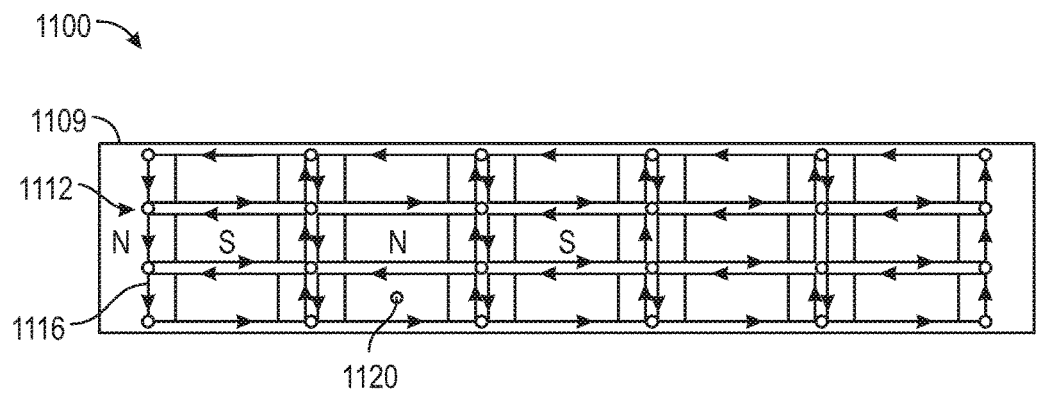

FIGS. 11A & 11B show schematic views illustrating coil alignment of an example EMAT device in accordance with embodiments of the present disclosure. Referring to FIG. 11A, EMAT device 1100 includes a coil array 1102 over a magnet array 1104. The magnet array is show as a linear Halbach array, but other magnet array configurations may also be used. The coil array 1102 comprises an array of coil loops 1106 laid out as a grid of rectangular coil loops proximate the first side of the magnet array. The coil loops 1106 of the array 1102 may be co-planar and/or overlapping with neighboring coils to reduce mutual inductance among coils.

Each coil loop of the array has a magnetic dipole moment opposing each of the magnetic dipole moments of any adjacent coil loops. This may be accomplished by a first group of the coil loops each have current flowing clockwise in the plane and a second group of the coil loops each have current flowing counter-clockwise in the plane.

In further aspects, the arrangement of coils can be altered for transmitters and receivers to obtain the most sensitivity to the response. For example, alignment of the coils with respect to the magnet arrays may be configured to take advantage of the flux patterns of a particular magnet array. A maximum of the magnetic flux on the first side of the magnet array may be centered on a particular magnet of the magnet array, such as the north- and south-aligned magnets of a linear Halbach array. A plurality of coils may include at least one transmitter coil having a first alignment with respect to the particular magnet; and at least one receiver coil having a second alignment with respect to the particular magnet different than the first alignment.

These alignments may be carried out in a single layer by leaving an area over the magnet area uncovered by coil. In the alternative, as described above with respect to FIG. 8A, EMAT devices may include a plurality of coils arranged as a multilayer coil assembly. The multilayer coil assembly may include separate sets of coils for transmitting and for receiving. Each layer may thus be configured or transmitting or receiving, both through the mode of electrical connection in the measurement circuit, as described above, and, as described below, via the alignment of transmitting and receiving layers.

For transmitters, where it is desirable to maximize the Lorentz force, the edge of the coils responsible for creating eddy currents in the casing in the direction of interest may be aligned with (e.g., directly over) the location of maximum magnetic flux (e.g., for a linear Halbach array, on top of N or S oriented magnets). On the other hand, the receiver coils measure the current in the coils due to change in magnetic field. This change comes from vibration of casing due to acoustic wave passing through the casing. As described in greater detail above, the acoustic wave itself is generated by Lorentz forces from the transmitter. In order for the receivers to have the maximum sensitivity to the vibration of the casing the center of coil should be at the location of maximum magnetic flux (e.g., for a linear Halbach array, on top of N or S oriented magnets). So, as described above, if each transducer is acting as both a transmitter and receiver, the device may be configured to switch between two sets of coils based on the transducer acting as a transmitter of receiver.

Returning to FIG. 11A, coil loops 1108 of the array 1102 are transmitter coils. Each transmitter coil comprises a perimeter. Portions 1110 of the perimeter which, upon activation of the measurement circuitry, predominantly produces eddy currents in the tubular along a longitudinal axis of the tubular is aligned with a maximum of magnetic flux from the array. Here that alignment is centered over the north- or south-aligned magnets of the array.

Referring to FIG. 11B, a coil array 1112 comprises an array of coil loops 1116 laid out as a grid of rectangular coil loops proximate the first side of the magnet array in a layer different than the layer of array 1102. The coil loops 1116 of the array 1112 may be co-planar. The coil loops 1116 are receiver coils having a center 1120 aligned with a maximum of magnetic flux from the array. Here that alignment is centered over the north- or south-aligned magnets of the array.

Figure 11C:
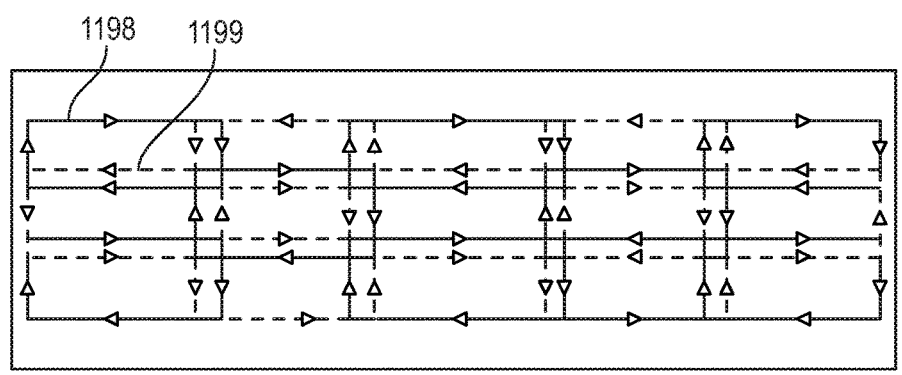
FIG. 11C shows co-planar adjacent coil configurations with overlapping coil border areas.

At least a first coil loop and a second coil loop of the array of coil loops may overlap. FIG. 11C shows co-planar adjacent coil configurations 1198 and 1199 with overlapping coil border areas. Optimal coil overlapping is used to minimize coupling between nearest-neighbor coils. See for example, Lopez et al. Overlap Decoupling in Hole-Slotted Arrays. *Proc. Intl. Soc. Mag. Reson. Med.* 18 (2010). Overlapping coil areas of adjacent coils as shown in FIG. 11C may result in cancellation of magnetic flux from each coil with a net flux density minimized towards zero in the common area at the border of alternating magnets. In particular applications, however, it may be desirable to have no overlapping between coils.

Figure 12A:
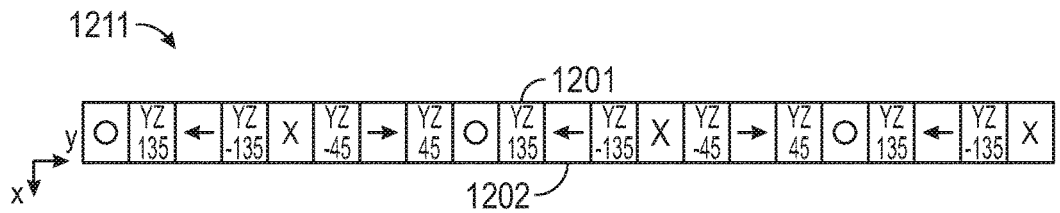
FIGS. 12A-12D illustrate example magnet configurations for EMAT devices in accordance with embodiments of the present disclosure.
Figure 12B:
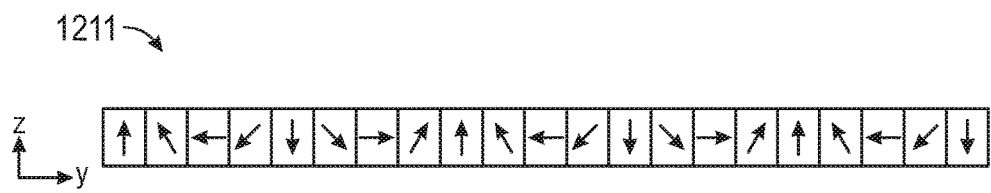
Figure 12C:
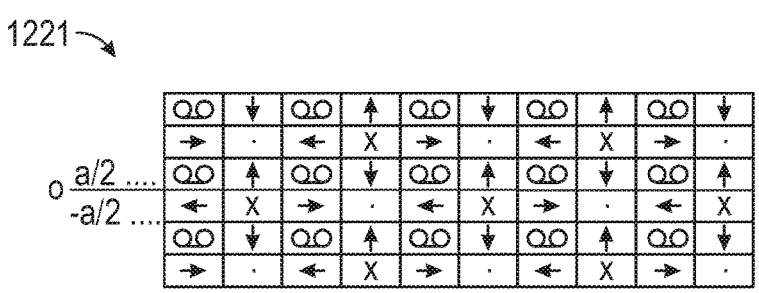
Figure 12D:
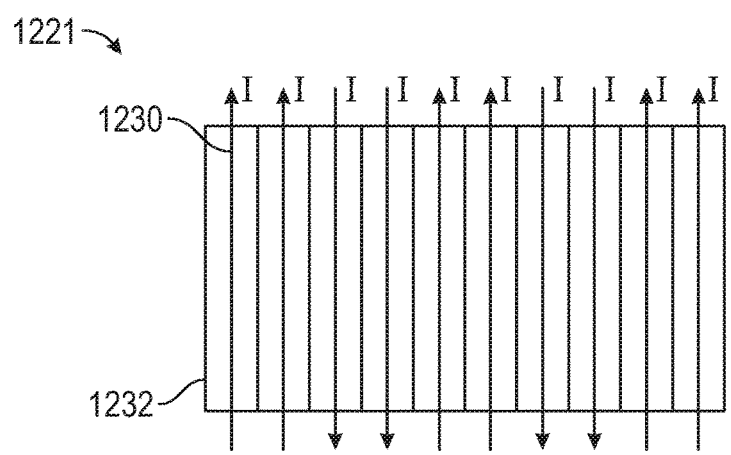

FIGS. 12A-12D illustrate example magnet configurations for EMAT devices in accordance with embodiments of the present disclosure. FIGS. 12A and 12B show a Halbach array 1211. The magnet array 1211 comprises magnets arranged with a corresponding direction of magnetization of a first magnet 1201 oriented at a 45 degree angle with respect to a corresponding direction of magnetization of a second magnet 1202. FIG. 12C shows a modified Halbach array 1221. The magnets 1206 of array 1221 have a width a. FIG. 12D shows current 1230 across the rows 1232 of the array 1221. The rows 1232 are centered on an x axis (1240). Array 1221 comprises rows of linear Halbach arrays with auxiliary magnet arrays between the linear Halbach arrays. Alternatively, looking forward to FIG. 12F, magnet blocks within the Halbach array 1211 with the same magnetization direction could be composed of laminated stacks 1233 oriented vertically in the Z-direction and along the Z-Y plane's coordinate orientations shown in FIGS. 12A and 12B. The magnet laminated stacks magnet assembly contribute to eddy currents reduction and improved design control of the orientation and directivity of the magnetic fields.

Figure 12E:
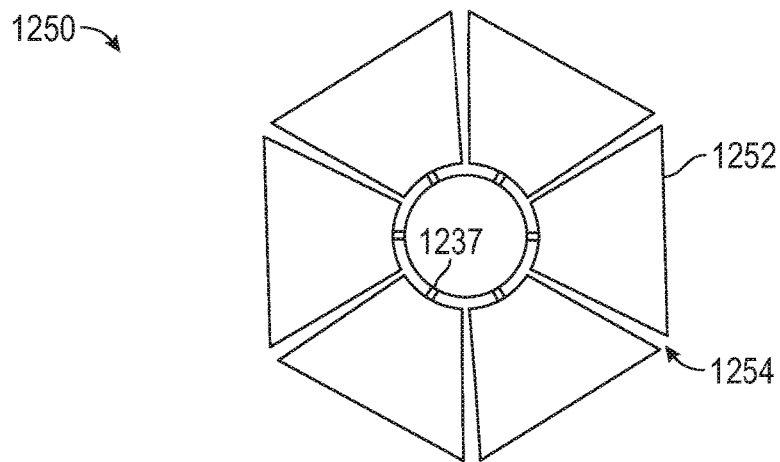
FIG. 12E shows a cross section of a downhole tool with six EMAT pads.

Because the instrument may be configured for a downhole tool, it may be advantageous to allow the curvature of the array to approximate the curvature of the borehole. FIG. 12E shows a cross section of a downhole tool 1250 with six EMAT pads 1252 each comprising a sensor. Each circumferentially (e.g., circularly) distributed sensor may be an individual Halbach magnet array 1211 (e.g., six total for the tool). Each array may be mounted on pads 1252 which may be retractable via arms 1237 towards the central longitudinal axis of the tool.

Each EMAT pad 1252 has an array 1254 in a modified Halbach configuration with a substantially trapezoidal or parallelogram cross-sectional geometry. It is desirable to minimize the downhole tool profile while maximizing the mass of the magnet array. This is particularly true in well installation applications, where constraints on tool size may be demanding. Tool 1250 optimizes this combination of factors.

Figure 12F:
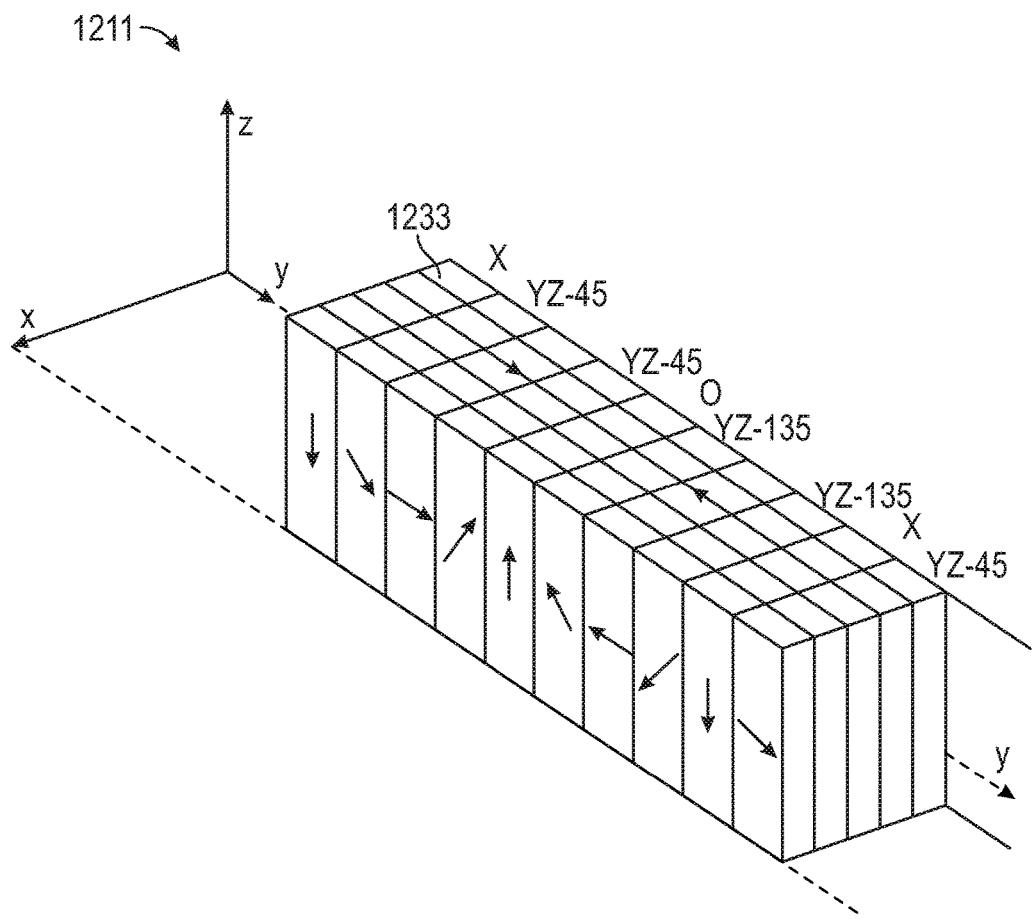
FIG. 12F shows a modified Halbach array showing an assembly with several magnet stacks.

FIG. 12F shows a modified Halbach array 1254 showing an assembly with several magnet stacks 1256, with the magnets of each stack aligned along a the x direction. The array 1254 may be configured as those arrays described in greater detail above, but being bowed in a radial direction toward the borehole wall. See the discussion with respect to FIG. 12B. Each adjacent stack may include magnets of magnetization directions gradually varying from the relationships of magnetization directions of the above examples. That is, in sequence, the direction of magnetization of each magnet in the stack is progressively further rotated than the previous magnet as though mapped to a curved surface.

In the place of any magnet described herein, a number of magnets having the same direction of magnetization or an equivalent aggregate direction of magnetization may be substituted. This may prevent eddie currents within a particular magnet, for example. Aggregating individual magnets is known.

Each stack (and each magnet, or group of magnets) may have a parallelogram or trapezoidal geometry cross-section for a better Halbach magnet assembly fit in order to achieve the desired final array profile. The gradual variation of magnetization direction and the magnet stack assembly can be designed to enhance the Halbach magnet characteristics to project the magnetic field toward a preferred direction with higher intensity.

Figure 13A:
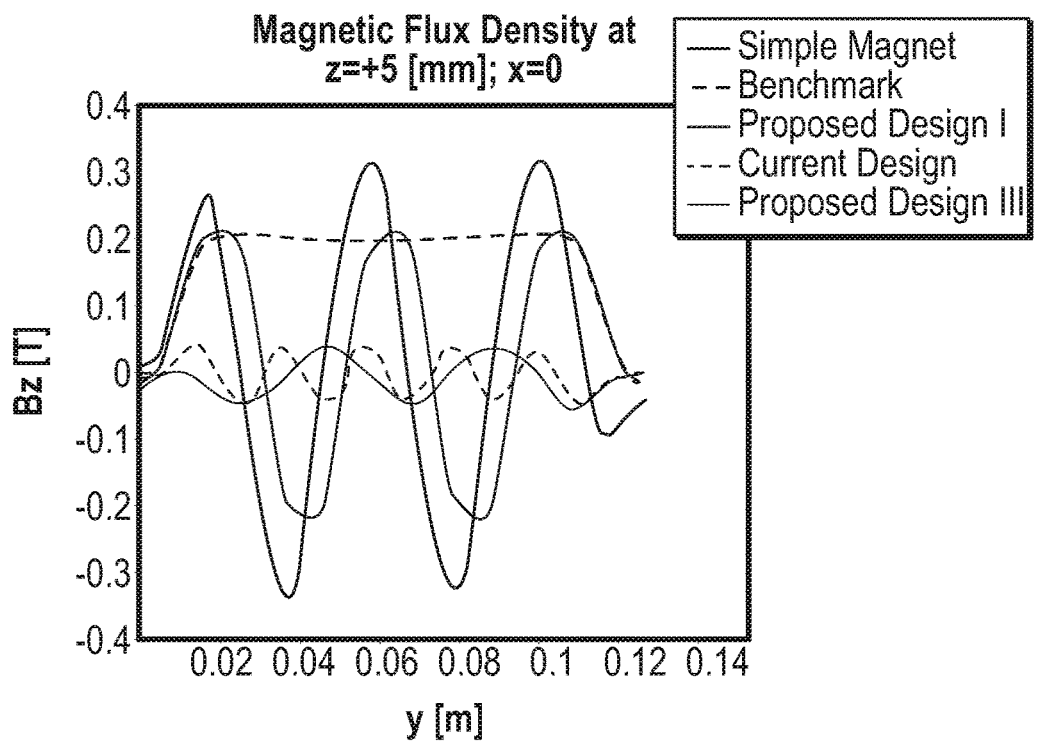
FIGS. 13A-13C illustrate the magnetic flux density at different locations about the face of various magnet arrays in accordance with embodiments of the present disclosure.
Figure 13B:
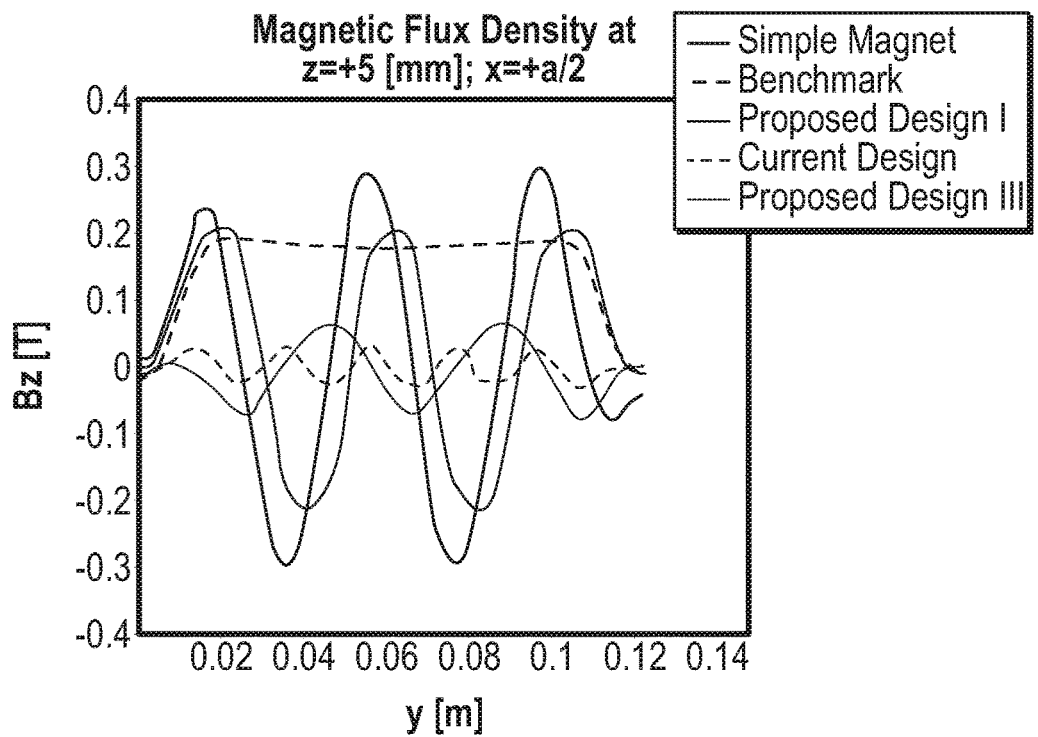
Figure 13C:
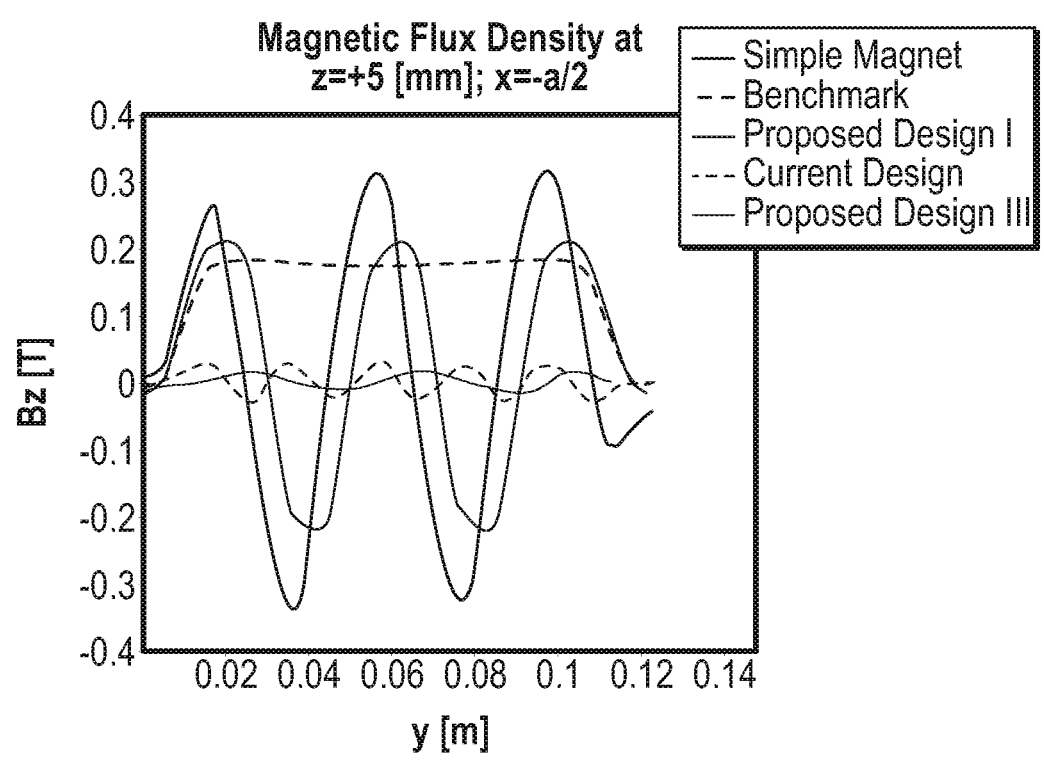

FIGS. 13A-13C illustrate the magnetic flux density at different locations about the face of various magnet arrays in accordance with embodiments of the present disclosure. FIG. 13A illustrates the magnetic flux density at z=+5 mm along the x axis (1240, FIG. 12C) with respect to distance across the array. FIG. 13B illustrates the magnetic flux density at z=+5 mm along the a/2 axis (1240, FIG. 12C) with respect to distance across the array. FIG. 13C illustrates the magnetic flux density at z=+5 mm along the −a/2 axis (1240, FIG. 12C) with respect to distance across the array. A comparison between strength of each magnet (Bz integrated over a fixed area in front of sensor) as calculated:

$$P = \int_A |Bz x_{,,}| dA$$

is shown in the Table below.

TABLE 1

| Magnet type | P [Wb] |
| --- | --- |
| Benchmark | 2.9e−4 |
| Device 1100 | 3.6e−4 |
| Linear Halbach | 5.1e−5 |
| Array 1221 | 7.2e−5 |
| Simple Magnet | 3.5e−4 |

Comparison of these results indicates that obtaining the desired alternation in force by changing the coil and magnet layout may be desirable. FIGS. 14A and 14B illustrate EMAT devices in accordance with embodiments of the present disclosure. The devices include magnets with passages from a first side of the magnet to a second opposing side. Thus, the wiring of the sensor array may be as close to the face of the magnet array as possible.

Herein, "information" may include raw data, processed data, analog signals, and digital signals. Estimation of the parameter may include the use of a model. In some embodiments, the model may include, but is not limited to, one or more of: (i) a mathematical equation, (ii) an algorithm, and so on. The at least one parameter of interest may include, but is not limited to, one or more of: (i) reflectance; (ii) transit time; (iii) an acoustic image of the borehole (e.g., geometry of the borehole); and so on.

In some aspects, this disclosure relates to estimating a parameter of interest related to a volume of an earth formation, such as, for example, an earth formation surrounding a borehole. The parameter of interest may be a physical characteristic of the volume, such as, for example, geometry.

The term "carrier" as used above means any device, device component, combination of devices, media and/or member that may be used to convey, house, support or otherwise facilitate the use of another device, device component, combination of devices, media and/or member. Exemplary non-limiting conveyance devices include drill strings of the coiled tube type, of the jointed pipe type and any combination or portion thereof. Other conveyance device examples include casing pipes, wirelines, wire line sondes, slickline sondes, drop shots, downhole subs, BHA's, drill string inserts, modules, internal housings and substrate portions thereof, self-propelled tractors. The term "processor" herein includes, but is not limited to, any device that transmits, receives, manipulates, converts, calculates, modulates, transposes, carries, stores or otherwise utilizes information. A processor refers to any circuitry performing the above, and may include a microprocessor, resident memory, and/or peripherals for executing programmed instructions, application specific integrated circuits (ASICs), field programmable gate arrays (FPGAs), or any other circuitry configured to execute logic to perform methods as described herein. The term "information" as used above includes any form of information (Analog, digital, EM, printed, etc.). In one example embodiment, a processor may include a microprocessor, resident memory, and peripherals for executing programmed instructions.

In several non-limiting aspects of the disclosure, a processor includes a computer that executes programmed instructions for performing various methods. These instructions may provide for equipment operation, control, data collection and analysis and other functions in addition to the functions described in this disclosure, and may be stored on a non-transitory machine-readable medium accessible to the processor. The non-transitory machine-readable medium may include ROMs, EPROMs, EAROMs, Flash Memories, Optical disks, and Hard disks. Thus, configuration of the processor may include operative connection with resident memory and peripherals for executing programmed instructions. The processor may execute instructions stored in computer memory accessible to the processor, or may alternatively employ logic implemented as field-programmable gate arrays ('FPGAs'), application-specific integrated circuits ('ASICs'), other combinatorial or sequential logic hardware, and so on. As noted above, the processing may be done downhole or at the surface, by using one or more processors. In addition, results of the processing, such as an image of an acoustic property or parameter values for a parameter of interest associated with a particular volume of interest (e.g., associated with a particular borehole depth), can be stored on a suitable medium.

The term "substantially real-time" as applied to methods of the present disclosure refers to an action performed (e.g., estimation, modeling, and so on) while the sensor is still downhole, after the generation of the information and prior to movement of the sensor an appreciable distance within the context of evaluating the borehole or formation at an associated resolution, such as, for example, a distance of 100 meters, 50 meters, 25 meters, 10 meters, or less; and may be defined as estimation of the parameter of interest or production of the current iteration of a model within 15 minutes of generating the information, within 10 minutes of generation, within 5 minutes of generation, within 3 minutes of generation, within 2 minutes of generation, within 1 minute of generation, or less. The term "substantially continuous" as applied to measurement in accordance with embodiments of the present disclosure means that no gaps exist within the measurement corresponding to a circumference of the borehole at a particular borehole depth.

Implicit in the processing of the data is the use of a computer program implemented on a suitable machine readable medium that enables the processor to perform the control and processing. The machine readable medium may include ROMs, EPROMs, EAROMs, Flash Memories and Optical disks. The determined formation properties may be recorded on a suitable medium and used for subsequent processing upon retrieval of the BHA. The determined formation properties may further be telemetered uphole for display and analysis.

While the foregoing disclosure is directed to the one mode embodiments of the disclosure, various modifications will be apparent to those skilled in the art. It is intended that all variations be embraced by the foregoing disclosure.

We claim:

1. An apparatus for evaluating a tubular, the apparatus comprising:
   a sensor including an electromagnetic acoustic transducer (EMAT) device configured to be conveyed into the tubular, the EMAT device comprising:
   measurement circuitry comprising at least one conductive coil including:
      at least one transmitter coil comprising multiple coil layers arranged in a stack and electrically connected in parallel, and
      at least one receiver coil electrically non-identical to the at least one transmitter coil; and
   a magnet array comprising magnets arranged with a corresponding direction of magnetization of each magnet oriented according to a configuration producing a greater magnetic flux on a first side of the array than on a second side opposing the first side.

2. The apparatus of claim 1, wherein the magnetic flux produced from the second side is substantially zero.

3. The apparatus of claim 1, wherein the configuration of magnets comprises at least a first set of permanent magnets in a linear Halbach configuration.

4. The apparatus of claim 1 wherein the at least one coil comprises:
- at least one transmitter coil; and
- at least one receiver coil electrically non-identical to the at least one transmitter coil.

5. The apparatus of claim 4 wherein an inductance of the at least one transmitter coil is lower than an inductance of the at least one receiver coil.

6. The apparatus of claim 1 wherein the at least one coil comprises a plurality of coils, and the measurement circuitry is configured to be switched between a transmit mode and a receive mode, wherein, while in the transmit mode, the measurement circuitry forms a first circuit optimized for transmission with at least some of the plurality of coils; and while in the receive mode, the measurement circuitry forms a second circuit optimized for reception with a portion of the plurality of coils.

7. The apparatus of claim 6 wherein, in the transmit mode, the plurality of coils comprises multiple coil layers electrically connected in parallel; and in the receive mode, the plurality of coils comprises the multiple coil layers electrically connected in series.

8. The apparatus of claim 1 wherein the EMAT device is further configured to form a wave within the tubular, the wave having a polarization that is that of at least one of (i) a compressional wave, (ii) a shear wave, (iii) a transversely polarized shear wave, (iv) a Lamb wave, and (v) a Rayleigh wave.

9. The apparatus of claim 1 wherein a maximum of the magnetic flux on the first side of the magnet array is centered on a particular magnet of the magnet array, and wherein the at least one coil comprises:
- at least one transmitter coil having a first alignment with respect to the particular magnet; and
- at least one receiver coil having a second alignment with respect to the particular magnet different than the first alignment.

10. The apparatus of claim 9 wherein the at least one transmitter coil comprises a perimeter, and a portion of the perimeter is aligned with the particular magnet.

11. The apparatus of claim 10 wherein, upon activation of the measurement circuitry, the portion of the perimeter predominantly produces eddy currents in the tubular along a longitudinal axis of the tubular.

12. The apparatus of claim 9 wherein the at least one receiver coil comprises a center, and the center is aligned with the particular magnet.

13. The apparatus of claim 9, wherein the at least one conductive coil comprises an array of coil loops wherein each coil loop of the array of coil loops has a magnetic dipole moment opposing each of the magnetic dipole moments of any adjacent coil loops of the array of coil loops.

14. The apparatus of claim 13, wherein the array of coil loops comprises a grid of rectangular coil loops proximate the first side of the magnet array.

15. The apparatus of claim 13, wherein at least a first coil loop and a second coil loop of the array of coil loops overlap such that mutual inductance between the first coil loop and the second coil loop is mitigated.

16. The apparatus of claim 1, wherein the magnet array comprises magnets arranged with a corresponding direction of magnetization of a first magnet oriented at a 45 degree angle with respect to a corresponding direction of magnetization of a second magnet.

17. The apparatus of claim 1, wherein the magnet array comprises a magnet block with a given magnetization direction including an assembly of lamination stacks.

18. An apparatus for evaluating a tubular, the apparatus comprising:
- a sensor including an electromagnetic acoustic transducer (EMAT) device configured to be conveyed into the tubular, the EMAT device comprising:
- measurement circuitry comprising at least one conductive coil; and
- a magnet array comprising magnets arranged with a corresponding direction of magnetization of each magnet oriented according to a configuration producing a greater magnetic flux on a first side of the array than on a second side opposing the first side;
- wherein the at least one conductive coil comprises an array of coil loops wherein each coil loop of the array of coil loops has a magnetic dipole moment opposing each of the magnetic dipole moments of any adjacent coil loops of the array of coil loops.

* * * * *